United States Patent
Bounyong et al.

(10) Patent No.: US 10,646,140 B2
(45) Date of Patent: May 12, 2020

(54) RISK-OF-FALLING DETERMINATION APPARATUS, RISK-OF-FALLING DETERMINATION METHOD, RECORDING MEDIUM, AND OUTPUT APPARATUS

(71) Applicant: Panasonic Intellectual Property Management Co., Ltd., Osaka (JP)

(72) Inventors: Souksakhone Bounyong, Nara (JP); Shinobu Adachi, Nara (JP); Jun Ozawa, Nara (JP); Misaka Kimura, Kyoto (JP); Yuya Watanabe, Kyoto (JP); Keiichi Yokoyama, Kyoto (JP)

(73) Assignee: Panasonic Intellectual Properly Management Co., Ltd., Osaka (JP)

( * ) Notice: Subject to any disclaimer, the term of this patent is extended or adjusted under 35 U.S.C. 154(b) by 599 days.

(21) Appl. No.: 15/392,907

(22) Filed: Dec. 28, 2016

(65) Prior Publication Data

US 2017/0196483 A1 Jul. 13, 2017

(30) Foreign Application Priority Data

Jan. 7, 2016 (JP) .................. 2016-001440

(51) Int. Cl.
*A61B 5/00* (2006.01)
*A61B 5/11* (2006.01)
(Continued)

(52) U.S. Cl.
CPC .......... *A61B 5/1117* (2013.01); *A61B 5/0492* (2013.01); *A61B 5/112* (2013.01);
(Continued)

(58) Field of Classification Search
CPC .......... A61B 5/0488; A61B 2562/0219; A61B 5/1118; A61B 5/746; A61B 5/1116;
(Continued)

(56) References Cited

U.S. PATENT DOCUMENTS

| 5,016,635 A | * | 5/1991 | Graupe | ................ | A61B 5/0488 |
| | | | | | 600/546 |
| 2005/0067816 A1 | * | 3/2005 | Buckman | ............. | A41D 13/018 |
| | | | | | 280/730.1 |

(Continued)

FOREIGN PATENT DOCUMENTS

JP  2010-172481  8/2010

OTHER PUBLICATIONS

Akira Ochi et al., "Leg muscle activity patterns for forward falling avoidance stepping in easily falling elderly people", The 48th Congress of Japanese Society of Physical Therapy (Nagoya), 2013 <URL: https://www.jstage.jst.go.jp/article/cjpt/2012/0/2012_48100485/_pdf>.

*Primary Examiner* — May A Abouelela
(74) *Attorney, Agent, or Firm* — Wenderoth, Lind & Ponack, L.L.P.

(57) ABSTRACT

A risk-of-falling determination apparatus includes a walk information obtainer that obtains walk information of a user, a myoelectric sensor that measures a first myoelectric potential difference on an anterior surface of a thigh of the user and a second myoelectric potential difference on a posterior surface of the thigh, a control circuit that identifies an interval of a stance phase by using the walk information, calculates a degree of co-contraction at a corresponding leg of the user on the basis of the first and second myoelectric potential differences for the stance phase, and determines whether the degree of co-contraction is greater than or equal to a first threshold, and an outputter that outputs a signal indicating that the user has a high risk of falling if the degree of co-contraction is greater than or equal to the first threshold.

11 Claims, 16 Drawing Sheets

(51) Int. Cl.
*G16H 50/30* (2018.01)
*G16H 50/20* (2018.01)
*A61B 5/0492* (2006.01)

(52) U.S. Cl.
CPC .......... *A61B 5/7275* (2013.01); *G16H 50/20* (2018.01); *G16H 50/30* (2018.01); *A61B 5/002* (2013.01); *A61B 5/7264* (2013.01); *A61B 5/7405* (2013.01); *A61B 2562/0219* (2013.01)

(58) Field of Classification Search
CPC ......... A61B 5/681; A61B 5/11; A61B 5/1117; A61B 5/1123; A61B 5/112; G16H 50/30; A61M 2230/60
USPC ............... 600/300, 301, 546, 587, 592, 595; 623/25; 340/870.01; 601/84
See application file for complete search history.

(56) References Cited

U.S. PATENT DOCUMENTS

| | | | | |
|---|---|---|---|---|
| 2005/0177059 A1* | 8/2005 | Koivumaa | ........... | A61B 5/0488 600/546 |
| 2006/0015470 A1* | 1/2006 | Lauer | ................... | A61B 5/0488 706/8 |
| 2007/0232869 A1* | 10/2007 | Kanzaki | ............. | A61B 5/04012 600/300 |
| 2008/0004904 A1* | 1/2008 | Tran | .................... | A61B 5/0006 705/2 |
| 2008/0161937 A1* | 7/2008 | Sankai | .................. | A61H 3/008 623/25 |
| 2008/0208287 A1* | 8/2008 | Palermo | ............... | A61N 1/0452 607/48 |
| 2008/0275309 A1* | 11/2008 | Stivoric | ................. | A61B 5/411 600/300 |
| 2011/0166491 A1* | 7/2011 | Sankai | ............... | A41D 13/1281 601/84 |
| 2012/0215076 A1* | 8/2012 | Yang | .................... | A61B 5/0205 600/301 |
| 2012/0245483 A1* | 9/2012 | Lundqvist | ............ | A61B 5/0492 600/546 |
| 2014/0070957 A1* | 3/2014 | Longinotti-Buitoni | ....................... A61B 5/6804 340/870.01 |
| 2014/0125491 A1* | 5/2014 | Park | ...................... | A61B 5/0205 340/870.01 |
| 2014/0191863 A1* | 7/2014 | Ten Kate | .............. | A61B 5/1116 340/539.12 |
| 2015/0182795 A1* | 7/2015 | Martikka | ........... | A63B 24/0062 340/870.07 |
| 2015/0250420 A1* | 9/2015 | Longinotti-Buitoni | ..................... A61B 5/6804 600/301 |
| 2015/0366504 A1* | 12/2015 | Connor | ................ | A61B 5/6804 600/301 |
| 2016/0121109 A1* | 5/2016 | Edgerton | ........... | A61N 1/36003 607/45 |
| 2016/0147959 A1* | 5/2016 | Mariottini | ............... | G16H 50/20 706/46 |
| 2016/0158033 A1* | 6/2016 | Hahn | ........................ | A61F 2/60 623/25 |
| 2016/0374618 A1* | 12/2016 | Giovangrandi | ...... | A61B 5/6887 600/393 |
| 2017/0196513 A1* | 7/2017 | Longinotti-Buitoni | ..................... A61B 5/6804 |
| 2017/0231490 A1* | 8/2017 | Toth | ........................ | A61B 5/40 600/558 |

* cited by examiner

RISK-OF-FALLING DETERMINATION APPARATUS, RISK-OF-FALLING DETERMINATION METHOD, RECORDING MEDIUM, AND OUTPUT APPARATUS

BACKGROUND

1. Technical Field

The present disclosure relates to an apparatus, a method, a recording medium, and an output apparatus for determining the risk of falling by using myoelectric potential differences.

2. Description of the Related Art

Methods for evaluating or determining the risk of falling have hitherto been proposed (see, for example, Japanese Unexamined Patent Application Publication No. 2010-172481 (hereinafter, referred to as PTL 1) and Akira Ochi and four others, "Itentou koureisha ni okeru zenpoutentou kaihi suteppu no kashikinkatsudou pataan", The 48th Congress of Japanese Society of Physical Therapy (Nagoya), <URL: https://www.jstage.jst.go.jp/article/cjpt/2012/0/2012_48100485/_pdf> (hereinafter, referred to NPL 1)). PTL 1 discloses a method for evaluating the risk of falling by measuring the dynamic balance and the lower limb muscular strength which relate to falling. In addition, NPL 1 discloses a relationship between the walking ability and the lower limb myoelectric potential differences.

However, the methods disclosed in PTL 1 and NPL 1 have issues in that the methods sometimes require time and effort and high determination accuracy is sometimes difficult to achieve.

SUMMARY

One non-limiting and exemplary embodiment provides a risk-of-falling determination apparatus or the like capable of determining the risk of falling simply with a high accuracy.

In one general aspect, the techniques disclosed here feature a risk-of-falling determination apparatus including a walk information obtainer that obtains walk information of a user for a predetermined time interval; a myoelectric sensor that measures a first myoelectric potential difference by using first electrodes disposed on an anterior surface of a thigh of a leg of the user and measures a second myoelectric potential difference by using second electrodes disposed on a posterior surface of the thigh of the leg of the user, the first myoelectric potential difference being a myoelectric potential difference on the anterior surface of the thigh, the second myoelectric potential difference being a myoelectric potential difference on the posterior surface of the thigh; a control circuit that (i) identifies an interval of a stance phase in the predetermined time interval by using the walk information of the user, the interval of the stance phase being an interval for which a foot of the leg of the user is in contact with ground, (ii) calculates a degree of co-contraction at the leg of the user by using the first myoelectric potential difference for the interval of the stance phase and the second myoelectric potential difference for the interval of the stance phase, the co-contraction being simultaneous activation of a muscle near the anterior surface of the thigh of the leg and a muscle near the posterior surface of the thigh of the leg, and (iii) determines whether the degree of co-contraction is greater than or equal to a first threshold; and an outputter that outputs a signal indicating that the user has a high risk of falling if the degree of co-contraction is greater than or equal to the first threshold.

The risk-of-falling determination apparatus according to the general aspect of the present disclosure is capable of determining the risk of falling simply with a high accuracy.

It should be noted that these general or specific embodiments may be implemented as a system, a method, an integrated circuit, a computer program, a computer-readable recording medium, or any selective combination thereof. Examples of the computer-readable recording medium include a non-volatile recording medium, for example, a Compact Disc-Read Only Memory (CD-ROM).

Additional benefits and advantages of the disclosed embodiments of the present disclosure will become apparent from the specification and drawings. The benefits and/or advantages may be individually provided by the various embodiments and features of the specification and drawings, which need not all be provided in order to obtain one or more of such benefits and/or advantages.

DETAILED DESCRIPTION

Figure 1A:
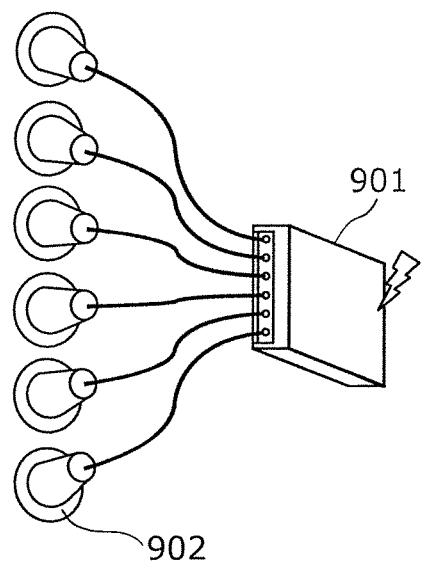
FIG. 1A is a diagram illustrating the external appearance of an electromyograph used in an experiment.

1. Underlying Knowledge Forming Basis of Present Disclosure

The inventors have found the following issues of the methods disclosed in PTL 1 and NPL 1, which are cited in the "BACKGROUND" section.

According to the method of PTL 1, each subject was classified into a high-fall-risk group or a low-fall-risk group on the basis of acceleration data obtained from the subject during exercise and during a walk. More specifically, receiver operating characteristic (ROC) analysis was performed on acceleration(s) produced in the up-down direction, the right-left direction, and/or the front-back direction of the body of each subject during an 8-second straight-line walking test and on the risk-of-falling indicator of the subject estimated based on a questionnaire or lower limb muscular strength to evaluate the risk of falling of the subject.

However, it is not clear whether the risks of falling of subjects having substantially the same physical strength data can be discriminately determined by using the method of PTL 1. That is, there may be cases where the risk of falling is not determined with a high accuracy.

In addition, according to the method of NPL 1, each subject who was an ambulatory elderly female was made to lean forward while having their back pulled by a traction cable (with a traction force of 20±2% of weight). Then, myoelectric potential differences were measured at the rectus femoris muscle, the vastus lateralis muscle, the biceps femoris muscle, the lateral head of the gastrocnemius muscle, and the tibialis anterior muscle of the subject in a condition where the subject moved their lower limb to step forward after the examiner released the traction. Further, each subject was classified into a fall group or a non-fall group depending on their fall history in the past year, and comparison of both groups was made. In this case, a result indicating that co-contraction of the rectus femoris muscle and the biceps femoris muscle of the fall group in the stepping phase was significantly high was obtained.

However, the method of NPL 1 is laborious not only for the subjects but also the evaluator or the examiner.

An experiment carried out by the inventors to cope with the issues described above and findings obtained from the experiment will be described prior to a description of an embodiment of the present disclosure.

1-1. Definition of Terms

Terms used in the present disclosure are defined first.

The term "co-contraction" refers to a state where an agonist muscle that causes a certain movement to occur and its antagonist muscle contract simultaneously. Since stiffness of a joint increases and a degree of freedom decreases in the state of co-contraction, smoothness of movement decreases. It is generally considered that co-contraction is more likely to occur for elderly people since the balance is achieved by activating more muscle fibers or stiffening the joint as the muscular strength or the balancing ability decreases due to aging.

The term "swing phase" refers to a time period for which a foot of interest is not in contact with the ground during a walk.

The term "stance phase" refers to a time period for which at least part of a foot of interest is in contact with the ground during a walk.

The term "one step" refers to a time period or interval from a time point at which a foot of interest leaves the ground to a time point at which the foot of interest leaves the ground again after the foot of interest comes into contact with the ground.

1-2. Point of View and Outline of Present Disclosure

The inventors focused on co-contraction of muscles as an indicator for determining the risk of falling. The inventors carried out an experiment to investigate a relationship between the risk of falling and a degree of co-contraction of lower limb muscles during a usual walking movement. Myoelectric potential differences on the anterior and posterior sides of the thigh and the lower leg were recorded for 52 elderly subjects while the subjects walked 5 meters in a straight line both ways three times, and the degree of co-contraction was calculated. As a result, the inventors found that it is possible to determine whether a subject has fall history in the past year at an accuracy of approximately 64% when the degree of co-contraction at the thigh in the stance phase during a walk is used as an indicator, even for subjects who have substantially the same physical strength data regarding the functional reach or the lower limb muscular strength, which is often used as an indicator of the risk of falling. Details of the experiment will be described below.

1-3. Details of Experiment

Figure 1B:
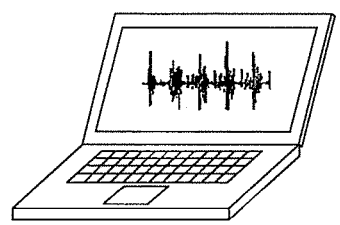
FIG. 1B is a diagram illustrating the external appearance of a display device used in the experiment.

FIGS. 1A and 1B illustrate the external appearance of an instrument and a device used in the experiment.

FIG. 1A illustrates the external appearance of an electromyograph used to measure myoelectric potential differences. The electromyograph includes a module 901 and electrodes 902. Each of the electrodes 902 is fixed to a site at which a myoelectric potential difference is desired to be measured. The module 901 processes signals received from the electrodes 902 and transmits transmission data to another device. The electrodes 902 and the module 901 are capable of communicating with each other via a cable or wirelessly. The display device having the external appearance illustrated in FIG. 1B receives transmission data from the electromyograph and displays a waveform or the like represented by the transmission data.

Figure 2:
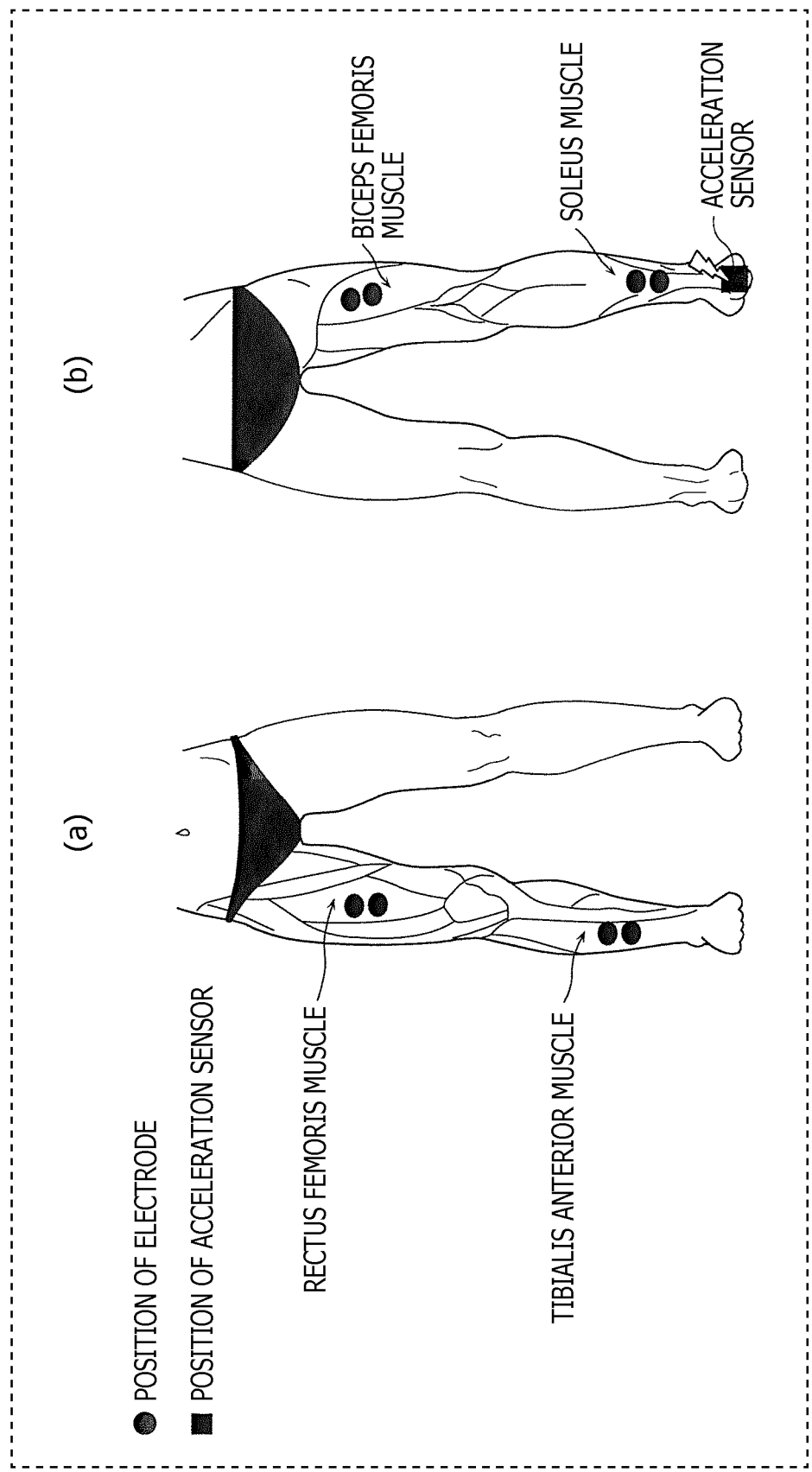
FIG. 2 is a diagram illustrating myoelectric potential measurement sites and an acceleration measurement site in the experiment.

FIG. 2 illustrates myoelectric potential measurement sites and an acceleration measurement site.

To measure myoelectric potential differences at a leg during a walk, the electrodes 902 of the electromyograph were attached to myoelectric potential measurement sites (sites indicated by black dots in FIG. 2) corresponding to four muscles (i.e., the rectus femoris muscle, the biceps femoris muscle, the tibialis anterior muscle, and the soleus muscle) as illustrated in FIG. 2. FIG. 2(*a*) illustrates the positions (i.e., myoelectric potential measurement sites) of the electrodes 902 attached on the anterior surface of the right leg of the subject above the rectus femoris muscle and the tibialis anterior muscle. FIG. 2(*b*) illustrates the positions of the electrodes 902 attached on the posterior surface of the right leg of the subject above the biceps femoris muscle and the soleus muscle. Although each of the electrodes 902 is just required to be located above a corresponding muscle of interest, each of the electrodes 902 may be located substantially at the center of the muscle of interest in the longitudinal direction of the muscle. Accordingly, two electrodes 902 among the electrodes 902 were disposed substantially at the center of the corresponding muscle of interest so that the two electrodes 902 were spaced apart by approximately 2 cm. That is, a potential difference between two sites that were above a muscle of interest and at which the two respective electrodes 902 were disposed was measured as a myoelectric potential difference at the muscle. In addition, the sampling frequency of the electromyograph was set to 1024 Hz, and a 15 Hz to 200 Hz band-pass filter was used.

To measure acceleration at the leg during a walk, an acceleration sensor was attached to the acceleration measurement site, i.e., the right heel of the subject.

1-4. Experiment Task

An experiment task will be described next.

Firstly, based on a questionnaire about fall history in the past year obtained in advance, subjects who have fall history were classified into a risk-of-falling group (high falling risk group) and subjects who do not have fall history were classified into a non-risk-of-falling group (low falling risk group).

During the myoelectric potential difference measurement experiment, myoelectric potential differences at the leg of subjects who walked 5 meters from the walk start position to the walk end position as usual were recorded. An experiment for measuring and recording such myoelectric potential differences is hereinafter referred to as a "5-meter walk experiment". Each subject was instructed to perform the "5-meter walk experiment" six times. Each subject was instructed to walk at their ordinary walking speed to the walk end position, which was 5 meters ahead.

1-5. Analysis Policy

Myoelectric data for each step was extracted from myoelectric data obtained by measurement performed using the electromyograph, on the basis of acceleration data obtained at the heel by measurement performed using the acceleration sensor. Note that the acceleration data is data representing a change in acceleration over time, and the myoelectric data is data representing a change in the myoelectric potential difference over time. The degree of co-contraction at the thigh and the degree of co-contraction at the lower leg were calculated on the basis of the extracted myoelectric data for each step, and relationships between the fall history and the degrees of co-contraction were investigated. Further, in more detailed analysis, the swing phase and the stance phase of each step were distinguished from each other on the basis of the acceleration data obtained at the heel, and relationships between the fall history and the degrees of co-contraction calculated for the respective phases were also investigated. A percentage of correctly determining subjects who have fall history to have a high risk of falling and correctly determining subjects who do not have fall history to have a low the risk of falling from among all the subjects was defined a percentage of correct determination. That is, the percentage of correct determination is calculated by using {(the number of subjects correctly determined to have a high risk of falling)+(the number of subjects correctly determined to have a low the risk of falling)}/the number of all the subjects. An optimum parameter used to determine the risk of falling was searched for on the basis of comparison of these percentages of correct determination.

1-6. Walking Cycle Detection Method

In the experiment, the swing phase and the stance phase of walking were distinguished from each other by using the data obtained by the acceleration sensor fixed to the right heel. The instrument used is not limited to the acceleration sensor, and a footswitch may be used. When a footswitch is used, a period for which the footswitch is pressed (period for which the foot is in contact with the ground) is determined to be the stance phase, and a period for which the footswitch is not pressed (period for which the foot is not in contact with the ground) is determined to be the swing phase. One swing phase and one stance phase following the swing phase constitute one cycle of walking (one walking cycle or one step).

Now, a specific method for determining the swing phase and the stance phase on the basis of the acceleration data obtained using the acceleration sensor attached to the heel will be described.

Figure 3:
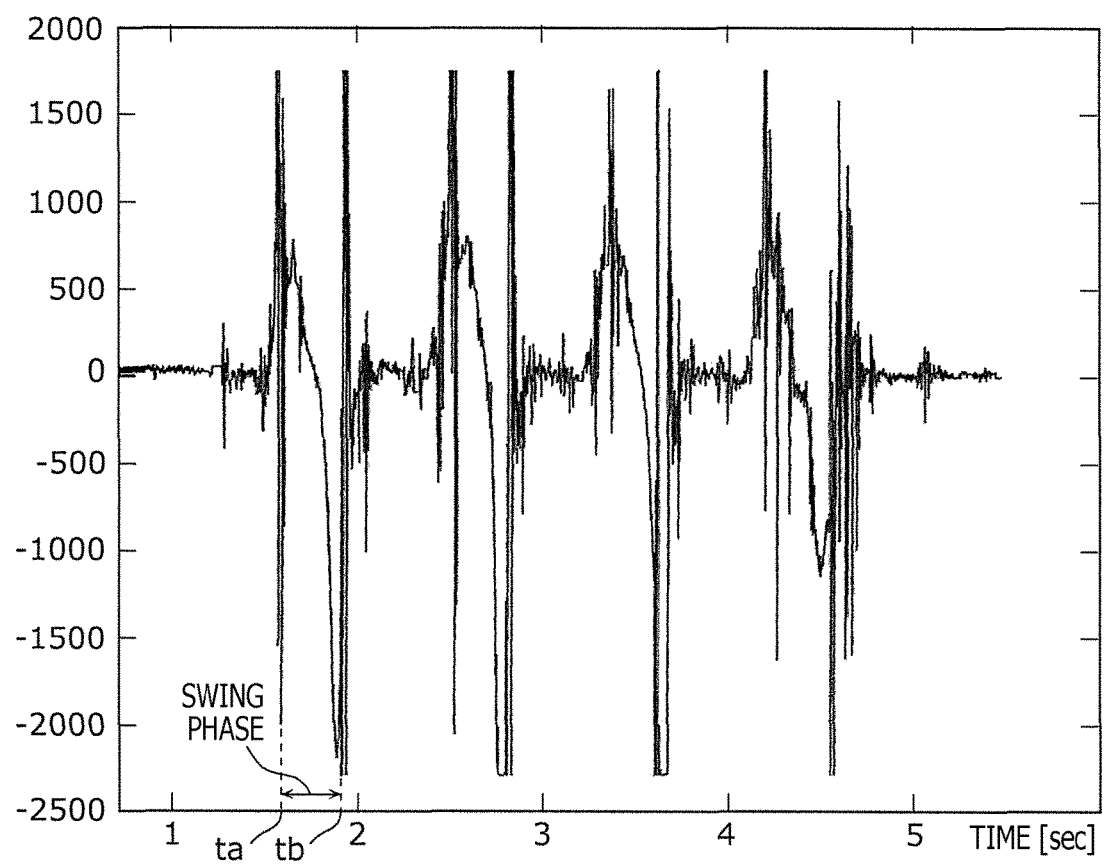
FIG. 3 is a diagram illustrating x-axis-direction acceleration data obtained by an acceleration sensor attached to the heel in the experiment.

FIG. 3 illustrates the x-axis-direction acceleration data obtained by the acceleration sensor attached to the heel. Note that the x-axis direction is the walking direction, and the positive direction in the x-axis direction is a direction in which the subject moves by walking. That is, acceleration illustrated in FIG. 3 is positive when the heel is accelerated in the direction in which the subject moves by walking and is negative when the heel is decelerated in that direction. FIG. 3 illustrates acceleration data for four steps. FIG. 3 indicates that acceleration at the heel cyclically changes in accordance with the walking rhythm. As illustrated in FIG. 3, the acceleration changes greatly around time ta at which the toe leaves the ground and around time tb at which the heel comes into contact with the ground. In addition, in the swing phase (from time ta to time tb), the acceleration changes smoothly toward the negative direction compared with the other time period. If these times ta and tb are successfully identified, the swing phase and the stance phase are successfully determined on the basis of the acceleration data.

To determine the swing phase and the stance phase, a low-pass filter was applied to the acceleration data illustrated in FIG. 3.

Figure 4:
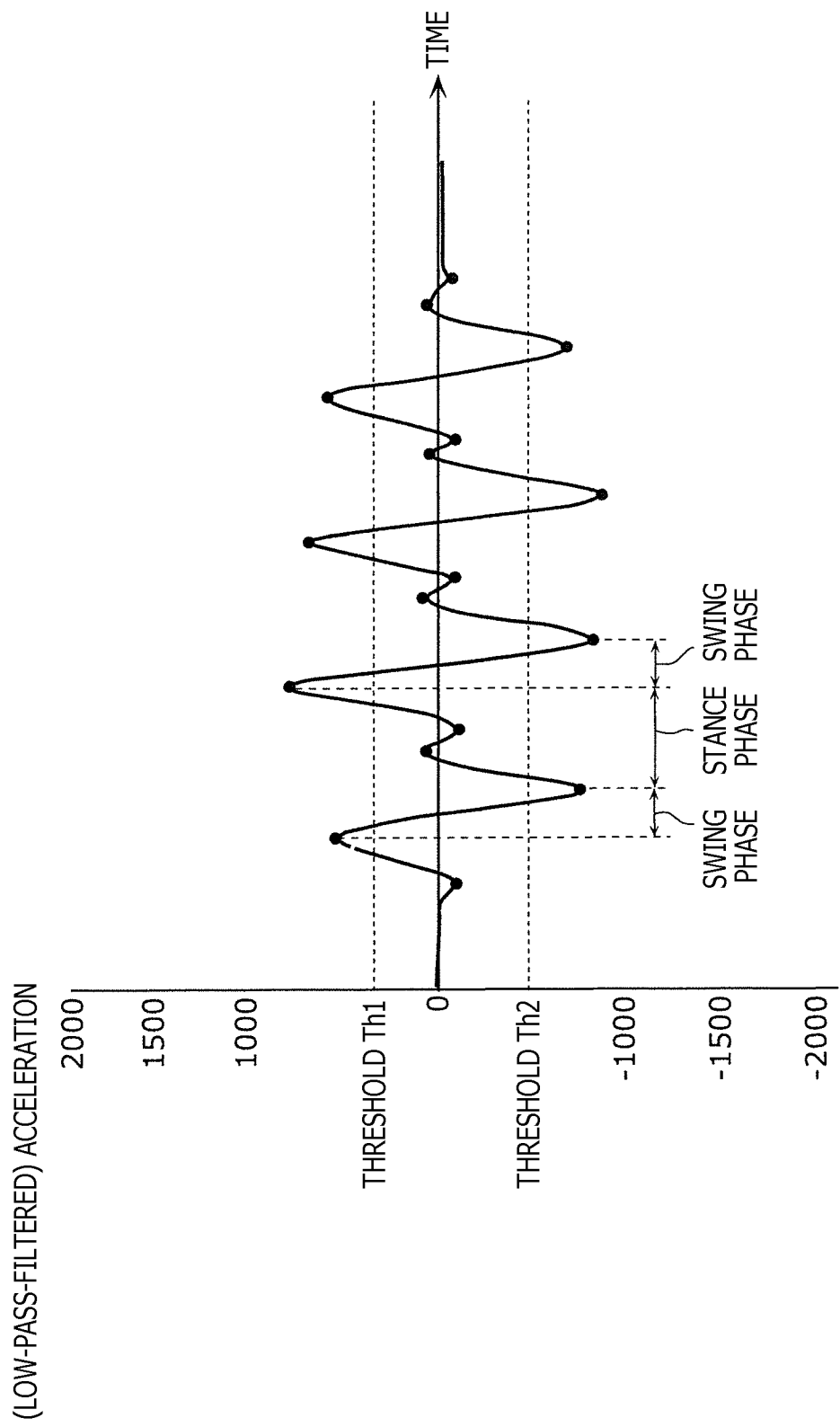
FIG. 4 is a diagram illustrating a result obtained by applying a low-pass filter to the acceleration data illustrated in FIG. 3.

FIG. 4 illustrates a result obtained by applying a 3 Hz low-pass filter to the acceleration data illustrated in FIG. 3. First, at least one peak in the positive direction and at least one peak in the negative direction are determined from the low-pass-filtered acceleration. The peak in the position direction is also referred to as a positive peak and indicates a local maximum acceleration. The peak in the negative direction is also referred to as a negative peak and indicates a local minimum acceleration. Then, thresholds Th1 and Th2 are set, and a peak greater than the threshold Th1 and a peak smaller than Th2 are respectively extracted from among the at least one positive peak and the at least one negative peak determined in the above manner. Then, the time of the peak greater than the threshold Th1 is determined as the start point of the swing phase, and the time of the peak smaller than the threshold Th2 is determined as the end point of the swing phase. In this way, the swing phase is identified first. Then, a time period from one swing phase to the next swing phase is determined as the stance phase. That is, the start point of the n-th stance phase is the sampling point immediately following the end point of the n-th swing phase, and the end point of the n-th stance phase is the sampling point immediately preceding the start point of the n+1-th swing phase.

Note that the swing phase and the stance phase can be determined on the basis of information other than acceleration. For example, in the case where a switch (footswitch)

attached to the heel or toe is used as described above, a time period for which the footswitch is on can be determined to be the stance phase, and a time period for which the footswitch is off can be determined to be the swing phase.

1-7. Calculation of Degree of Co-contraction

A method for calculating the degree of co-contraction of muscles will be described next.

Full-wave rectification, envelope detection, and normalization were performed on the entire myoelectric data obtained by measurement performed using the electromyograph. The normalization was performed on a walking cycle basis. Specifically, an average of envelope values of the myoelectric potential difference in the respective walking cycles determined by the walking cycle detection method described above was calculated, and a ratio of the envelope value of the myoelectric potential difference at each time point to the calculated average was determined. In this way, normalization was performed. Note that the waveform output from the electromyograph may be input to a full-wave rectification circuit, a waveform output from the full-wave rectification circuit may be input to an envelope detection circuit, and the above-described normalization may be performed on a waveform output from the envelope detection circuit.

Then, the degree of co-contraction was calculated by using Equations (1a), (1b), and (1c) below.

$$CI = \frac{2I_{ant}}{I_{total}} \quad (1a)$$

$$I_{ant} = \int_{t_1}^{t_2} EMG_b(t)dt + \int_{t_2}^{t_3} EMG_a(t)dt \quad (1b)$$

$$I_{total} = \int_{t_1}^{t_3} [EMG_a + EMG_b](t)dt \quad (1c)$$

Figure 5:
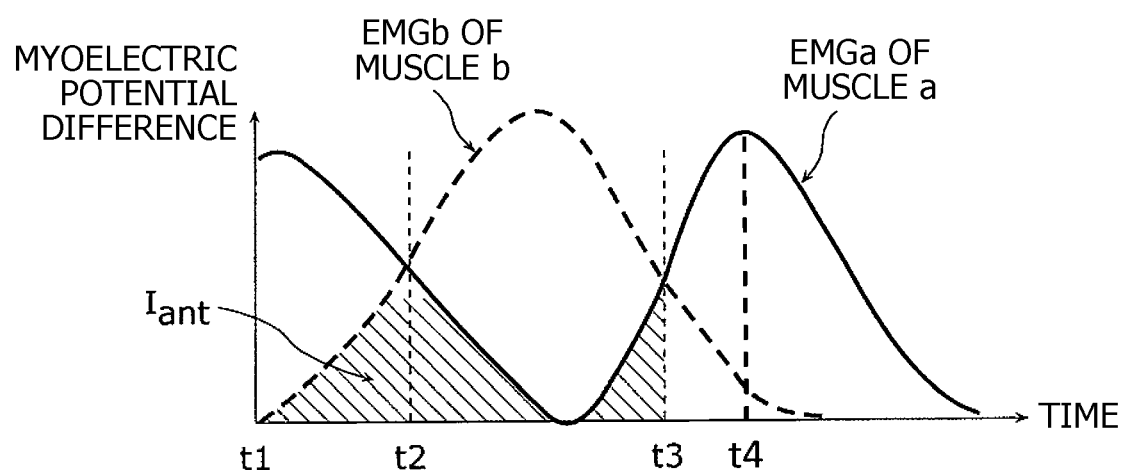
FIG. 5 is a diagram for describing a method for calculating a degree of co-contraction of muscles in the experiment.

FIG. 5 is a diagram for describing the method for calculating the degree of co-contraction of muscles a and b. Specifically, FIG. 5 illustrates waveforms ($EMG_a$ for the muscle a and $EMG_b$ for the muscle b) obtained by performing full-wave rectification, envelope derivation, and normalization on myoelectric data of the muscle a and myoelectric data of the muscle b.

In Equation (1a), CI represents the degree of co-contraction of the muscles a and b. In Equations (1b) and (1c), $EMG_a$ represents data (waveform) obtained by performing full-wave rectification, envelope detection, and normalization on the myoelectric data (waveform) of the muscle a, whereas $EMG_b$ represents data (waveform) obtained by performing full-wave rectification, envelope detection, and normalization on the myoelectric data (waveform) of the muscle b. In Equation (1b), $I_{ant}$ represents an integral value (area of the hatched portion in FIG. 5) of the myoelectric potential difference for an interval in which the antagonist muscle has worked (interval in which the antagonist muscle has worked in the stance phase). In FIG. 5, one walking cycle is from time point t1 to time point t4, and the stance phase is from the time point t1 to time point t3. As illustrated in FIG. 5, a period from the time point t1 to the time point t2 is an interval in which $EMG_b$ is below $EMG_a$, and a period from the time point t2 to the time point t3 is an interval in which $EMG_a$ is below $EMG_b$. In Equation (1c), $I_{total}$ represents the sum of the integral value of $EMG_a$ during movement (stance period) and the integral value of $EMG_b$ during movement (stance period). The degree of co-contraction CI at the thigh is obtained on the basis of the data $EMG_a$, which is obtained by performing full-wave rectification, envelope detection, and normalization on myoelectric data (waveform) obtained on the anterior side of the thigh (quadriceps femoris muscle), and the data $EMG_b$, which is obtained by performing full-wave rectification, envelope detection, and normalization on myoelectric data (waveform) obtained on the posterior side of the thigh (hamstrings muscle). In addition, the degree of co-contraction at the lower leg is obtained on the basis of the data $EMG_a$, which is obtained by performing full-wave rectification, envelope detection, and normalization on myoelectric data (waveform) obtained on the anterior side of the lower leg (tibialis anterior muscle or the like), and the data $EMG_b$, which is obtained by performing full-wave rectification, envelope detection, and normalization on myoelectric data (waveform) obtained on the posterior side of the lower leg (gastrocnemius muscle, soleus muscle, or the like). A normalization processing circuit may be provided, and the normalization process may be performed by the normalization processing circuit. An integral value calculation circuit may be provided, and the aforementioned integral values may be calculated by the integral value calculation circuit.

Note that the threshold was set to 62% in this experiment. If the degree of co-contraction CI of a subject is greater than or equal to the threshold, the subject is determined to have a high risk of falling. If the degree of co-concentration CI of a subject is less than the threshold, the subject is determined to have a low the risk of falling.

1-8. Excluded Data

Note that acceleration data of a subject for which each step was not correctly detectable due to mixture of noise to the acceleration data obtained at the heel was excluded from the analysis target. In addition, the data for which root-mean square (RMS) of the myoelectric potential difference extracted for each step included a value of +200 µV or greater or a value of −200 µV or smaller was determined to contain noise in the myoelectric potential difference, and such data was excluded from the analysis target.

1-9. Entire Interval and Steady State

During the data analysis process, the inventors found that characteristics of data for the first and last steps of walking differ from those of data for the rest of the steps in a period for which steady walking is continued. Accordingly, analysis was performed separately for the "entire interval" in which co-contraction for the entire 5-meter walk including the first and last steps was used and for the "steady state" in which co-contraction for the steady walking period excluding the first and last steps was used.

1-10. Calculation of Percentage of Correct Determination

The number of usable steps differs from subject to subject because of a difference between strides of the subjects and the number of excluded data items. Accordingly, the inventors regulated the number of additions by using a bootstrap method and determined the risk of falling by using linear discriminant based on data of co-contraction resulting from addition averaging. The bootstrap method is a method for extracting, for example, M samples at random from among N samples while permitting duplicates. The linear discriminant was derived by learning data of co-contraction and fall history of other people.

The discriminant analysis was performed by using the analysis-target interval (the entire interval or the steady state), the analysis-target unit (the swing phase, the stance phase, or both the swing phase and the stance phase), and the site (the thigh, the lower leg, or both the thigh and the lower leg) as parameters.

1-11. Experiment Result

An experiment result will be described below.

Figure 6A:
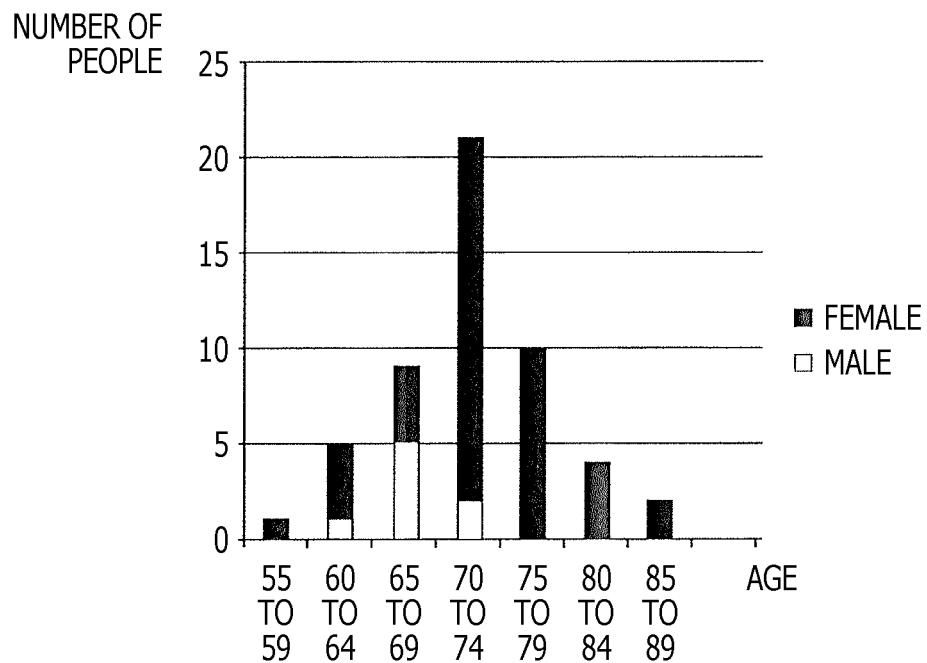
FIG. 6A is a diagram illustrating an age distribution of subjects of the experiment.
Figure 6B:
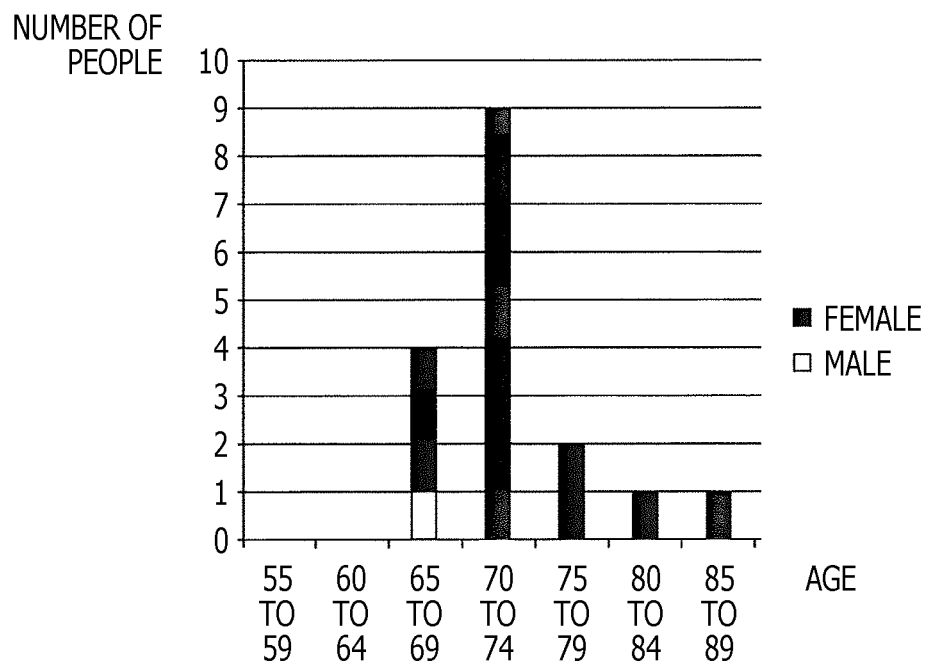
FIG. 6B is a diagram illustrating an age distribution of subjects of the experiment who have fall history.

FIGS. 6A and 6B respectively illustrate an age distribution of the subjects and an age distribution of subjects having fall history. FIG. 6A illustrates the age distribution of all participants who are the subjects. The participants were 52 subjects in total, and the number of participants in their early seventies was the largest (9 males and 43 females, average age of 72.3±6.1). In addition, FIG. 6B illustrates an age distribution obtained by extracting subjects having fall history (fall group). A group not having fall history in the past year (non-fall group) included 35 (including 8 males) subjects whose average age was 71.6±6.5. On the other hand, the group having fall history (fall group) included 17 (including 1 male) subjects whose average age was 73.6±5.2. When the significance level is set to 5%, no significant difference was recognized in terms of the ages of the fall group and the non-fall group.

Figure 7A:
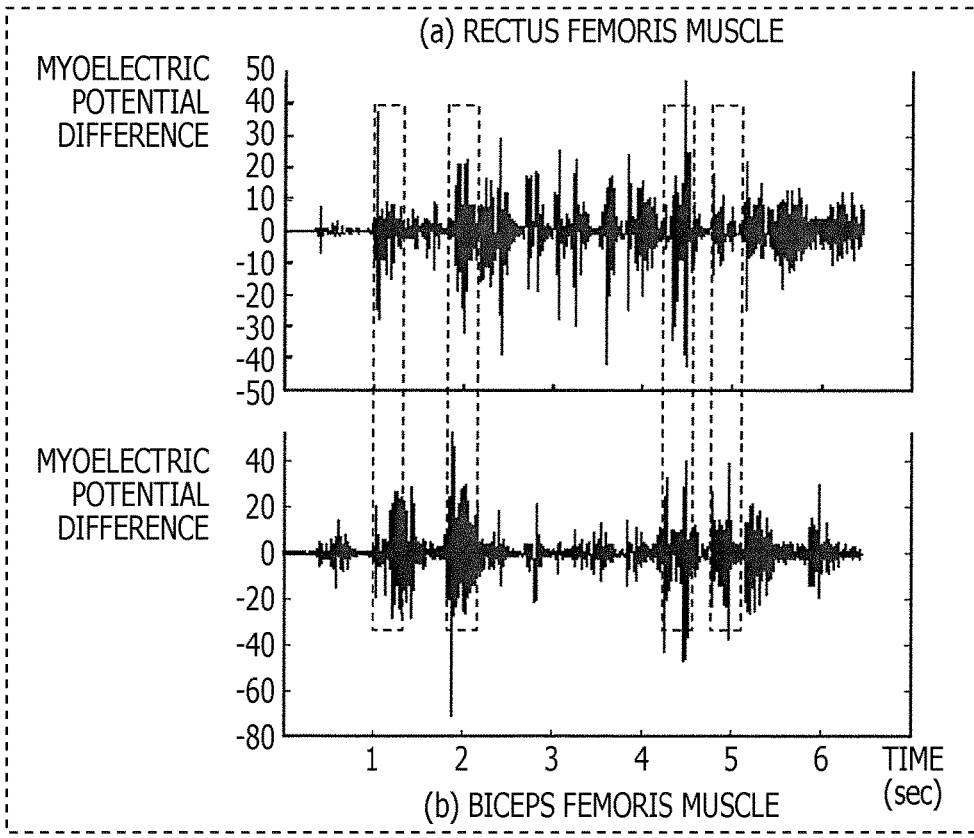
FIG. 7A is a diagram illustrating waveforms of myoelectric potential differences measured at the rectus femoris muscle and the biceps femoris muscle in the experiment.
Figure 7B:
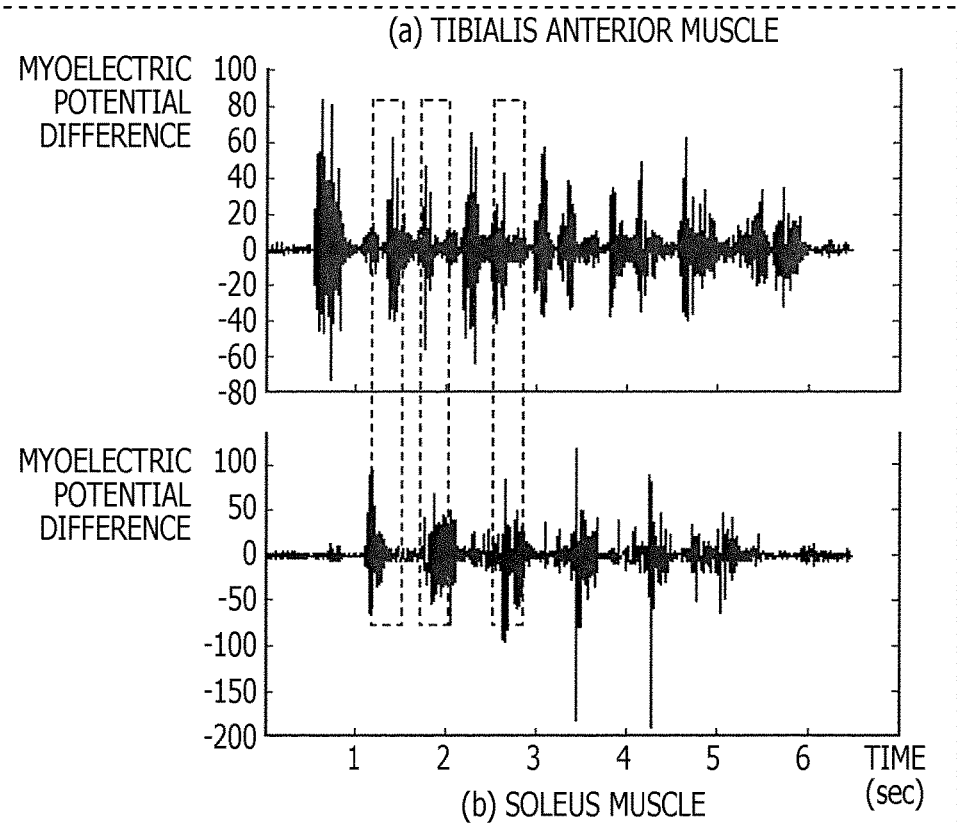
FIG. 7B is a diagram illustrating waveforms of myoelectric potential differences measured at the tibialis anterior muscle and the soleus muscle in the experiment.

Each of FIGS. 7A and 7B illustrates examples of waveforms of myoelectric potential differences measured by using an electromyograph during a walk. Specifically, FIG. 7A(a) illustrates a waveform of the myoelectric potential difference at the rectus femoris muscle (on the anterior side of the thigh), whereas FIG. 7A(b) illustrates a waveform of the myoelectric potential difference at the biceps femoris muscle (on the posterior side of the thigh). FIG. 7B(a) illustrates a waveform of the myoelectric potential difference at the tibialis anterior muscle (on the anterior side of the lower leg), whereas FIG. 7B(b) illustrates a waveform of the myoelectric potential difference at the soleus muscle (on the posterior side of the lower leg). In FIGS. 7A and 7B, a range where co-contraction occurs is surrounded by a dash line.

There were 28 subjects not having fall history for whom effective data of 10 or more steps was obtained from a total of 30-meter walk (5-meter walk experiment×6 times), and there were 14 subjects having fall history for whom such effective data was obtained. The average of the effective numbers of steps was 21.8±5.3 steps.

1-12. Analysis-Target Interval

The risk-of-falling determination result will be described below on the basis of a result obtained by performing addition averaging on co-contraction data for 10 steps by using the bootstrap method.

The risk of falling was determined for the entire interval by using co-contraction at the thigh, co-contraction at the lower leg, and co-contraction at both the thigh and the lower leg as respective parameters, and an average percentage of correct determination was derived for each case. Likewise, the risk of falling was determined for the steady state by using co-contraction at the thigh, co-contraction at the lower leg, and co-contraction at both the thigh and the lower leg as respective parameters, and an average percentage of correct determination was derived for each case.

Figure 8:
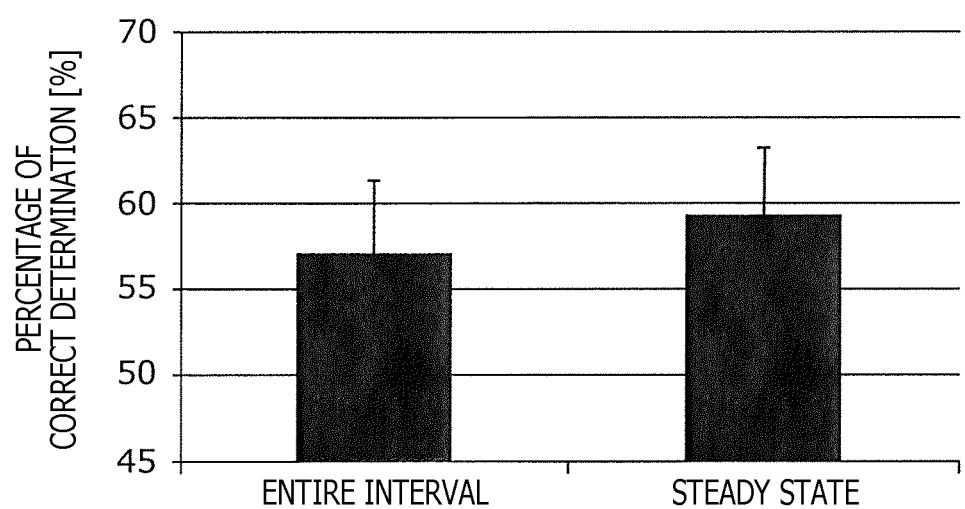
FIG. 8 is a diagram illustrating an average percentage of correct determination for the entire interval and an average percentage of correct determination for the steady state which are derived in the experiment.

FIG. 8 illustrates the average percentage of correct determination for the entire interval and the average percentage of correct determination for the steady state, which were determined in the above-described manner.

The average percentage of correct determination for the entire interval was 57.1±4.3%, whereas the average percentage of correct determination for the steady state was 59.4±4.0%. That is, the average percentage of correct determination for the steady state was significantly higher than that for the entire state. Accordingly, it is considered that the accuracy in the risk-of-falling determination increases if data obtained in the steady state excluding data for the first and last steps is used to determine the risk of falling based on co-contraction at the lower limb. This was a result obtained by the inventors for the first time by analyzing data obtained in the steady state.

Figure 9:
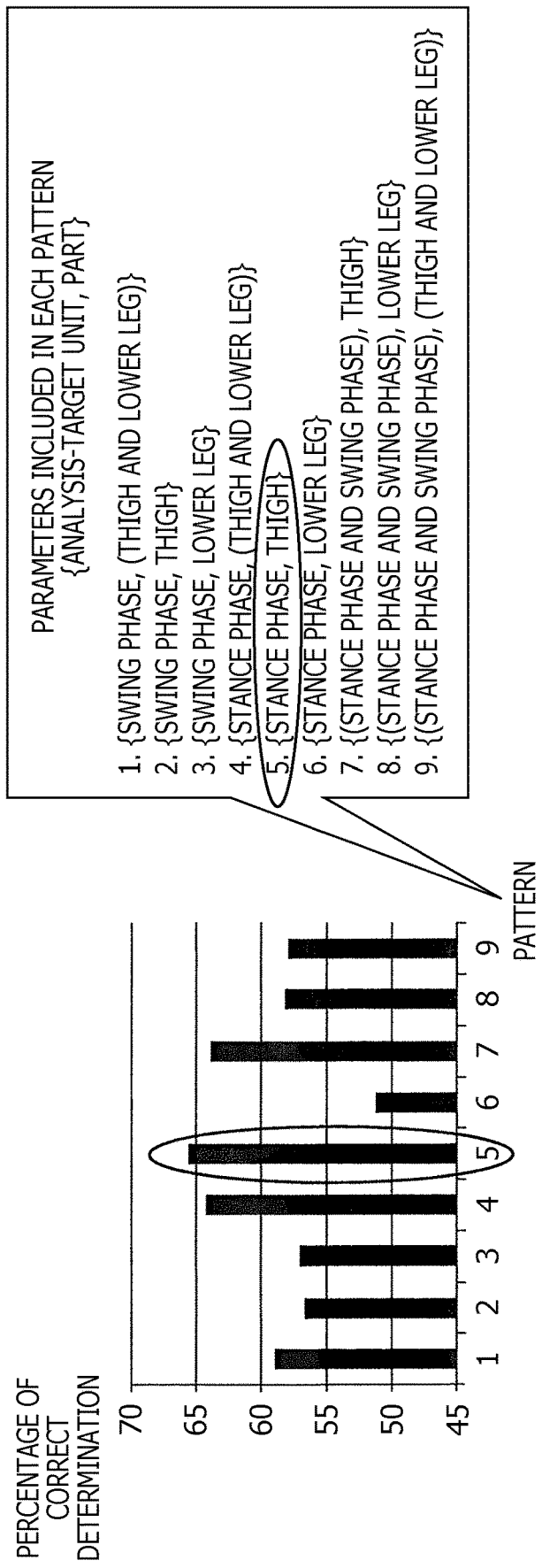
FIG. 9 is a diagram illustrating the percentages of correct determination each corresponding to one of nine patterns in the steady state derived in the experiment.

FIG. 9 illustrates the percentage of correct determination for each of nine patterns in the steady state. Each of the nine patterns includes the analysis-target unit and the site described above as the parameters. A pattern 1 is {analysis-target unit, site}={swing phase, (thigh and lower leg)}. A pattern 2 is {analysis-target unit, site}={swing phase, thigh}. A pattern 3 is {analysis-target unit, site}={swing phase, lower leg}. A pattern 4 is {analysis-target unit, site}={stance phase, (thigh and lower leg)}. A pattern 5 is {analysis-target unit, site}={stance phase, thigh}. A pattern 6 is {analysis-target unit, site}={stance phase, lower leg}. A pattern 7 is {analysis-target unit, site}={(stance phase and swing phase), thigh}. A pattern 8 is {analysis-target unit, site}={(stance phase and swing phase), lower leg}. A pattern 9 is {analysis-target unit, site}={(stance phase and swing phase), (thigh and lower leg)}.

The percentage of correct determination was 58.9% in the case of the pattern 1, 56.6% in the case of the pattern 2, 57.1% in the case of the pattern 3, 64.2% in the case of the pattern 4, and 65.6% in the case of the pattern 5. In addition, the percentage of correct determination was 51.3% in the case of the pattern 6, 63.8% in the case of the pattern 7, 58.1% in the case of the pattern 8, and 57.9% in the case of the pattern 9.

The percentage of correct determination was 61.1% in the case where data for each step obtained at the thigh was used, 56.5% in the case where data for each step obtained at the lower leg was used, and 61.3% in the case where data for each step obtained at the thigh and the lower leg was used.

The pattern for which the percentage of correct determination was the highest among the patterns 1 to 9 illustrated in FIG. 9 was the pattern 5 that uses the degree of co-contraction at the thigh in the stance phase as the feature quantity. FIG. 9 indicates that the percentage of correction determination is higher when the degree of co-contraction at the thigh was used as the feature quantity than when the degree of co-contraction at the lower leg alone was used as the feature quantity.

The above result has revealed that the percentage of correct determination based on analysis using addition averaging of data for 10 steps increases if the degree of co-contraction at the thigh in the stance phase is used as the feature quantity in the case where the swing phase and the stance phase are distinguished from each other in the steady state.

To investigate how many steps of data are needed to determine the risk of falling, a relationship between the number of times of addition and the percentage of correct determination was further investigated.

Figure 10:
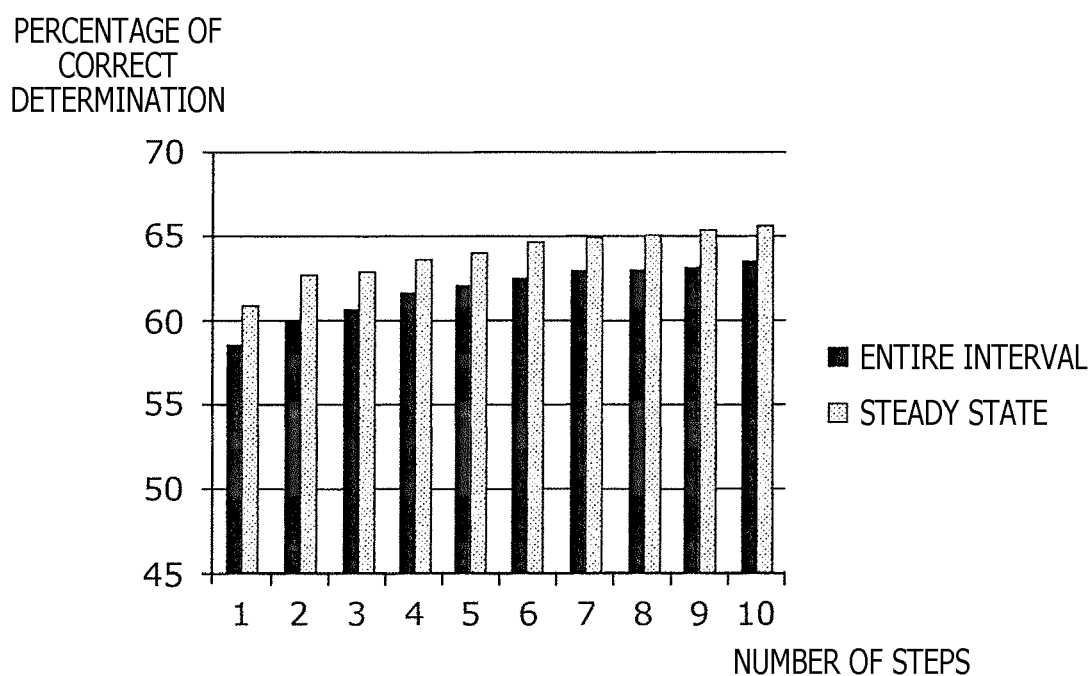
FIG. 10 is a diagram illustrating a relationship between the number of steps used in addition averaging and the percentage of correct determination for the entire interval and a relationship between the number of steps used in addition averaging and the percentage of correct determination for the steady state derived in the experiment.

FIG. 10 illustrates the relationship between the number of steps used in addition averaging and the percentage of correct determination for the entire interval and the relationship between the number of steps and the percentage of correct determination for the steady state. That is, FIG. 10 illustrates a change in the percentage of correction determination obtained when the degree of co-contraction at the thigh in the stance phase, which yields the highest percentage of correct determination in FIG. 9, was used as the feature quantity. In addition, FIG. 10 illustrates the percentage of correct determination obtained when the analysis-target interval is the steady state and the percentage of correct determination obtained when the analysis-target interval is the entire interval. FIG. 10 indicates that the percentage of correct determination of 60.9% can be achieved from data of one step in the steady state. Accordingly, the risk of falling that instantly changes during a walk is successfully determined for each step by using this method.

1-13. Summary of Findings Obtained from Experiment

The above-described results indicate that if the degree of co-contraction at the thigh in the stance phase of the steady state is used, a risk-of-falling determination accuracy of 65% or higher is achieved. Even if the degree of co-contraction at the thigh in the stance phase of the entire interval instead of the steady state is used, a risk-of-falling determination accuracy of about 63% is achieved. In addition, if the degree of co-contraction for at least two or more steps is calculated in a simpler manner without imposing any load on the user, a risk-of-falling determination accuracy of 60% or higher is achieved.

A risk-of-falling determination apparatus according to an aspect of the present disclosure based on such findings includes a walk information obtainer that obtains walk information of a user for a predetermined time interval; a myoelectric sensor that measures a first myoelectric potential difference by using first electrodes disposed on an anterior surface of a thigh of a leg of the user and measures a second myoelectric potential difference by using second electrodes disposed on a posterior surface of the thigh of the leg of the user, the first myoelectric potential difference being a myoelectric potential difference on the anterior surface of the thigh, the second myoelectric potential difference being a myoelectric potential difference on the posterior surface of the thigh; a control circuit that (i) identifies an interval of a stance phase in the predetermined time interval by using the walk information of the user, the interval of the stance phase being an interval for which a foot of the leg of the user is in contact with ground, (ii) calculates a degree of co-contraction at the leg of the user by using the first myoelectric potential difference for the interval of the stance phase and the second myoelectric potential difference for the interval of the stance phase, the co-contraction being simultaneous activation of a muscle near the anterior surface of the thigh of the leg and a muscle near the posterior surface of the thigh of the leg, and (iii) determines whether the degree of co-contraction is greater than or equal to a first threshold; and an outputter that outputs a signal indicating that the user has a high risk of falling if the degree of co-contraction is greater than or equal to the first threshold.

With this configuration, the user's risk of falling is successfully determined at an accuracy of 60% or higher as described in the "1-13. Summary of Findings Obtained from Experiment" section. In addition, since there is no need to use special physical strength data to determine the risk of falling, the risk of falling is successfully determined at the accuracy when such determination is performed for subjects having substantially the same physical strength data. Further, since the risk of falling is determined when the subject walks, the risk of falling is successfully determined in a simple manner without requiring the time and effort of the subject and the evaluator or the examiner. That is, the risk of falling is successfully determined simply with a high accuracy. In other words, the risk of falling during a walk can be determined highly accurately for individual users having substantially the same physical strength data by performing a simple measurement.

In addition, the walk information obtainer may be an acceleration sensor that is disposed on the leg of the user and that measures acceleration at the leg of the user for the predetermined time interval, and the control circuit may identify the interval of the stance phase in the predetermined time interval on the basis of a value of the acceleration in the (i).

With this configuration, since how acceleration at the leg changes in the stance phase differs from that of the swing phase, an interval of the stance phase is successfully identified appropriately by distinguishing the swing phase and the stance phase from each other.

In addition, in the (i), the control circuit may identify a first time point and a second time point in the predetermined time interval, the first time point being a time point at which the acceleration that is greater than or equal to a second threshold indicates a local maximum, the second time point being a time point that is later than the first time point and at which the acceleration that is smaller than or equal to a third threshold indicates a local minimum, and may identify, as the interval of the stance phase, an interval based on the first time point and the second time point or a remaining interval obtained by excluding the interval based on the first time point and the second time point from the predetermined time interval. For example, the control circuit may determine that the remaining interval is the interval of the stance phase if acceleration produced when the leg of the user is accelerated in a direction in which the user moves by walking is considered to be positive acceleration.

With this configuration, an interval of the stance phase is successfully identified appropriately.

In addition, the walk information obtainer may be a footswitch disposed on a back of the foot of the user, and the control circuit may identify an interval for which the footswitch is on as the interval of the stance phase in the predetermined time interval in the (i).

With this configuration, an interval of the stance phase can be identified reliably.

An output apparatus according to one disclosed aspect includes a first myoelectric sensor that is attached on skin above quadriceps femoris muscle of a thigh and outputs a first myoelectric potential signal; a second myoelectric sensor that is attached on skin above hamstrings muscle of the thigh and outputs a second myoelectric potential signal, a distance between the first myoelectric sensor and the quadriceps femoris muscle being smaller than a distance between the first myoelectric sensor and the hamstrings muscle, a distance between the second myoelectric sensor and the quadriceps femoris muscle being larger than a distance between the second myoelectric sensor and the hamstrings muscle; a control circuit that determines whether a first addition value and a second addition value satisfy a predetermined relationship.

An embodiment will be described specifically below with reference to the accompanying drawings.

The embodiment described below provides a general or specific example. The values, shapes, materials, components, arranged positions and connections of the components, steps, orders of the steps, etc., given in the following embodiment are merely illustrative, and are not intended to limit the present disclosure. In addition, among the components in the following embodiment, a component not recited in any of the independent claims indicating the most generic concept is described as an optional component.

2. Embodiment

Figure 11:
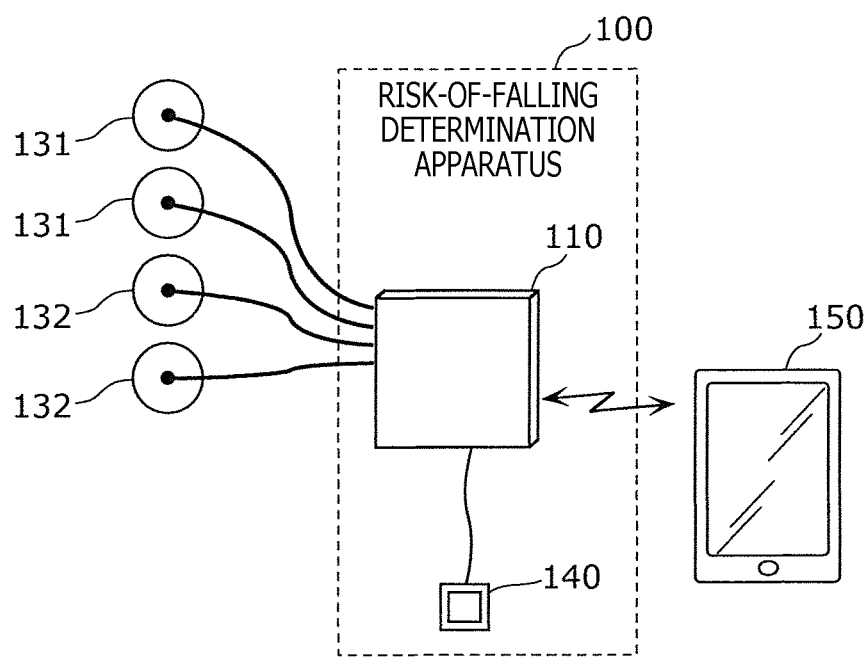
FIG. 11 is a diagram illustrating an example of the external appearance of a risk-of-falling determination apparatus according to an embodiment.

FIG. 11 illustrates an example of an external configuration of a risk-of-falling determination apparatus 100 according to an embodiment.

The risk-of-falling determination apparatus 100 includes a processing unit 110 and a walk information obtaining unit 140. The walk information obtaining unit 140 obtains, as walk information, information regarding a walk of the user who is a subject.

The processing unit 110 determines the risk of falling of the user who is a subject, by using a first myoelectric potential difference obtained from a pair of first electrodes 131, a second myoelectric potential difference obtained from a pair of second electrodes 132, and the walk information obtained by the walk information obtaining unit 140. That is, the processing unit 110 determines whether the user's risk of falling is high. The processing unit 110 then outputs the determination result to a terminal apparatus 150, for example, a smartphone, a tablet terminal, or a personal computer.

The processing unit 110 is connected to the walk information obtaining unit 140 wirelessly or by a cable. Likewise, the processing unit 110 is connected to the terminal apparatus 150 wirelessly or by a cable.

Figure 12:
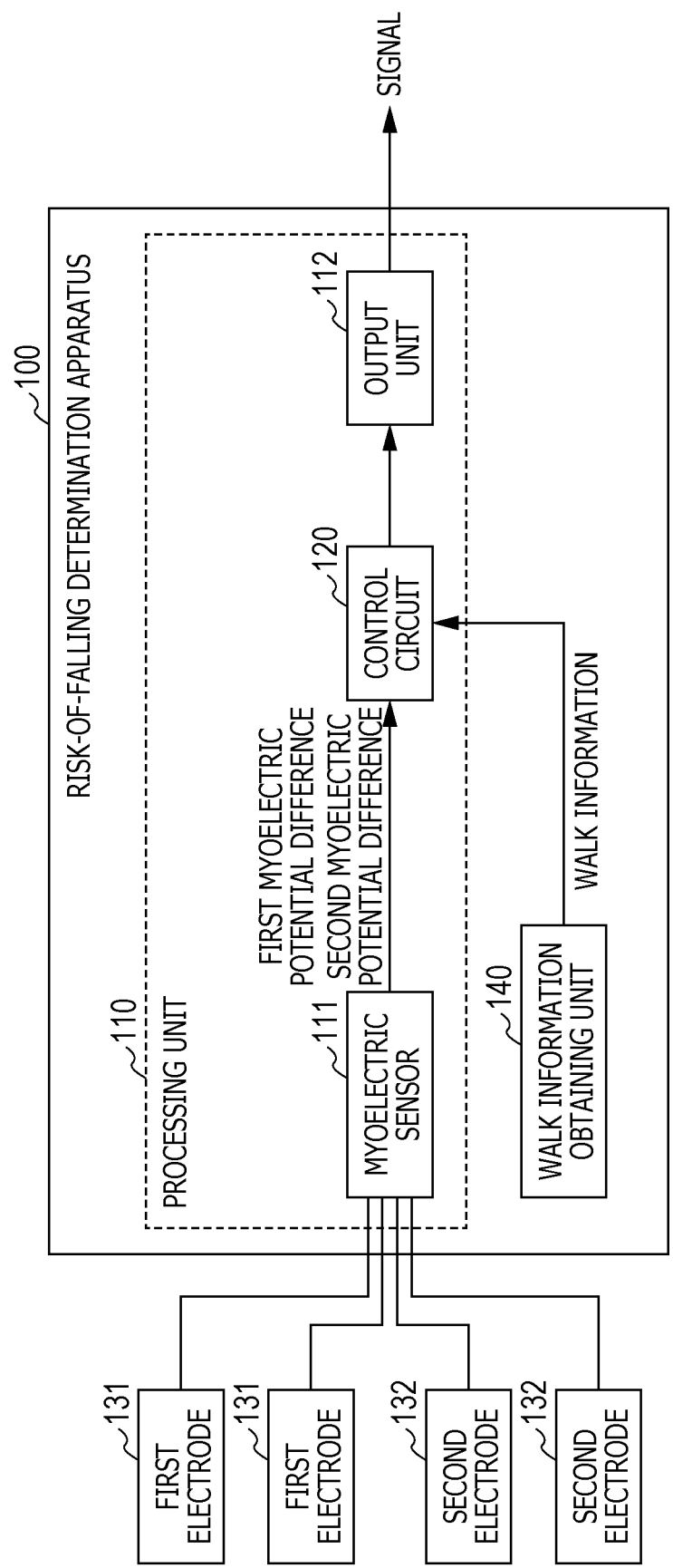
FIG. 12 is a block diagram illustrating an example of a functional configuration of the risk-of-falling determination apparatus according to the embodiment.

FIG. 12 is a block diagram illustrating an example of a functional configuration of the risk-of-falling determination apparatus 100.

The risk-of-falling determination apparatus 100 includes the walk information obtaining unit 140, a myoelectric sensor 111, a control circuit 120, and an output unit 112.

The walk information obtaining unit 140 obtains walk information of the user for a predetermined time interval. The walk information obtaining unit 140 may be, for example, an acceleration sensor or a footswitch described above. If the walk information obtaining unit 140 is an acceleration sensor, the walk information is, for example, the acceleration data illustrated in FIG. 3. If the walk information obtaining unit 140 is a footswitch, the walk information is, for example, a signal indicating on/off of the footswitch.

The myoelectric sensor 111 measures a first myoelectric potential difference, which is a myoelectric potential difference on the anterior surface of the thigh of a leg of the user, by using the pair of first electrodes 131 disposed on the anterior surface of the thigh. The myoelectric sensor 111 also measures a second myoelectric potential difference, which is a myoelectric potential difference on the posterior surface of the thigh of the leg of the user, by using the pair of second electrodes 132 disposed on the posterior side of the thigh. For example, the pair of first electrodes 131 are disposed above the quadriceps femoris muscle including the rectus femoris muscle, and the pair of second electrodes 132 are disposed above the hamstrings muscle including the biceps femoris muscle, as illustrated in FIG. 2.

The control circuit 120 identifies an interval of the stance phase in the predetermined time period, by using the walk information of the user. The interval of the stance phase is an interval for which the corresponding foot of the user is in contact with the ground. The control circuit 120 also calculates the degree of co-contraction at the corresponding one of legs of the user on the basis of the first myoelectric potential difference and the second myoelectric potential difference for the interval of the stance phase. Co-contraction refers to simultaneous activation of both a muscle on the anterior side of a thigh of a leg and a muscle on the posterior side of the thigh of the leg. In addition, the control circuit 120 determines whether the degree of co-contraction is larger than or equal to a first threshold. The first threshold may be, for example, 62%.

The output unit 112 outputs a signal indicating that the user has a high risk of falling if the degree of co-contraction is larger than or equal to the first threshold. For example, the output unit 112 outputs the signal to the terminal apparatus 150 via a wireless communication network. Upon receipt of the signal, the terminal apparatus 150 notifies the user of details indicated by the signal, that is, the user's high risk of falling by using sound or an image. Alternatively, the terminal apparatus 150 may store the signal on a recording medium, such as a memory, or transmit the signal to a server via a wired or wireless communication network.

Figure 13:
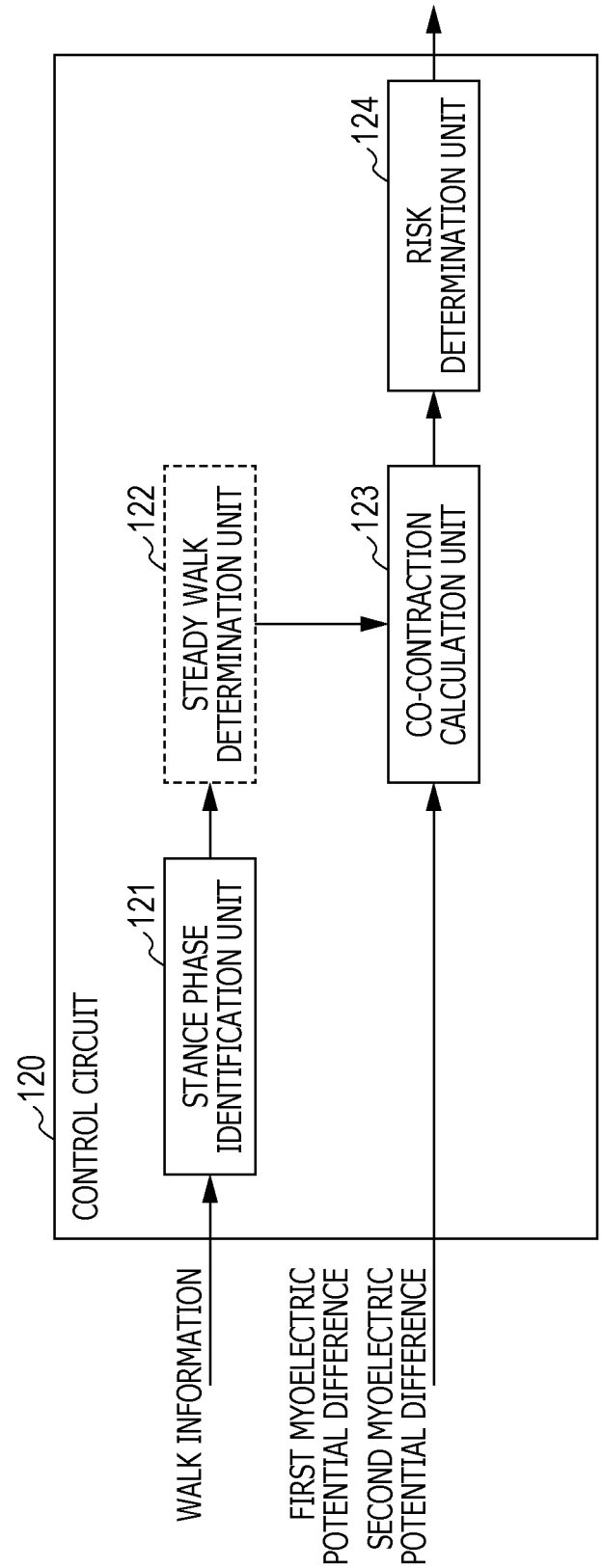
FIG. 13 is a block diagram illustrating an example of a functional configuration of a control circuit according to the embodiment.

FIG. 13 is a block diagram illustrating an example of a functional configuration of the control circuit 120.

The control circuit 120 includes a stance phase identification unit 121, a steady walk determination unit 122, a co-contraction calculation unit 123, and a risk determination unit 124.

The stance phase identification unit 121 identifies an interval of the stance phase included in the predetermined time interval by using walk information of the user. The predetermined time interval may be, for example, an interval of one step or one walking cycle.

Specifically, the stance phase identification unit 121 determines whether the user is walking by using the walk information. When acceleration data is used as the walk information, the stance phase identification unit 121 determines that the user is not walking if acceleration does not change for a predetermined period or more; otherwise, the stance phase identification unit 121 determines that the user is walking. When a signal indicating on/off of a footswitch is used as the walk information, the stance phase identification unit 121 determines that the user is not walking if switching between on and off does not occur for a predetermined period or more; otherwise, the stance phase identification unit 121 determines that the user is walking. The predetermined period may be, for example, one second.

Upon determining that the user is walking, the stance phase identification unit 121 identifies each walking cycle, divides the walking cycle into an interval of the swing phase and an interval of the stance phase, and detects the start timing and the end timing of each of the intervals. Such detection is performed by using the detection method described in the "Walking Cycle Detection Method" section. In this way, the intervals of the stance phase are identified.

As described above, an acceleration sensor or a footswitch, which serves as the walk information obtaining unit 140, is used to distinguish the swing phase and the stance phase from each other as described above. If a footswitch is used, the stance phase identification unit 121 identifies a time period for which the footswitch is pressed (the foot is in contact with the ground, i.e., the footswitch is on) as the interval of the stance phase. In addition, the stance phase identification unit 121 identifies a time period for which the footswitch is not pressed (the foot is not in contact with the ground, i.e., the footswitch is off) as the interval of the swing phase.

As described above, if the walk information obtaining unit 140 is an acceleration sensor, the stance phase identification unit 121 of the control circuit 120 identifies an interval of the stance phase in a predetermined time interval on the basis of the value of acceleration in this embodiment. The acceleration sensor is disposed on one of legs of the user and measures acceleration at the leg of the user for the predetermined time interval. The predetermined time interval may be, for example, an interval for one step or one walking cycle.

Specifically, the stance phase identification unit 121 of the control circuit 120 identifies a first time point and a second time point in the predetermined time interval. The first time point is a time point at which the acceleration that is greater than or equal to a second threshold indicates the local maximum. The second time point is a time point that is later than the first time point and at which the acceleration that is less than or equal to a third threshold indicates the local minimum. The second and third thresholds may be, for example, the thresholds Th1 and Th2 illustrated in FIG. 4, respectively. In addition, the local maximum and the local minimum are the positive peak and the negative peak, respectively. The stance phase identification unit 121 identifies, as the interval of the stance phase, an interval based on the first and second time points or a remaining interval obtained by excluding the interval based on the first and second time points from the predetermined time interval. If it is assumed that an acceleration of the case where one of legs of the user is accelerated in a direction in which the user moves by walking is a positive acceleration, the stance phase identification unit 121 of the control circuit 120 identifies the remaining interval as the interval of the stance phase.

In this way, the interval of the stance phase is successfully identified appropriately.

If the walk information obtaining unit 140 is a footswitch disposed on the back of a foot of the user, the stance phase identification unit 121 of the control circuit 120 identifies an interval for which the footswitch is on as the interval of the stance phase in the predetermined time interval in this embodiment.

In this way, the interval of the stance phase is successfully identified reliably.

If a plurality of intervals of the stance phase are identified by the stance phase identification unit 121, the steady walk determination unit 122 determines whether each of the plurality of intervals of the stance phase is an interval of the stance phase when the user is performing steady walking. The steady walk determination unit 122 extracts the intervals of the stance phase for which steady walking is performed from among the plurality of identified intervals of the stance phase. For example, the steady walk determination unit 122 extracts, as an interval of the stance phase in the steady state, at least one interval of the stance phase from among the rest of the identified series of intervals of the stance phase excluding the first and last stance phases.

The co-contraction calculation unit 123 calculates the degree of co-contraction at one of the legs of the user on the basis of the first myoelectric potential difference for an interval of the stance phase and the second myoelectric potential difference for the interval of the stance phase. For example, the co-contraction calculation unit 123 calculates the degree of co-contraction by using at least one interval of the stance phase extracted by the steady walk determination unit 122. That is, the co-contraction calculation unit 123 calculates the degree of co-contraction at the thigh in the steady state. A specific method used to calculate the degree of co-contraction is as described in the "Calculation of Degree of Co-contraction" section. That is, the co-contraction calculation unit 123 calculates the degree of co-contraction by performing addition averaging, full-wave rectification, envelope detection, and normalization on the myoelectric data for each interval of the stance phase and calculations represented by Equations (1a) to (1c).

The risk determination unit 124 determines whether the degree of co-contraction is greater than or equal to the first threshold. The first threshold may be, for example, 62%. The risk determination unit 124 then notifies the output unit 112 of the determination result.

The control circuit 120 includes the steady walk determination unit 122 in the example illustrated in FIG. 13; however, the control circuit 120 need not include the steady walk determination unit 122. In this case, the co-contraction calculation unit 123 calculates the degree of co-contraction at a thigh for the entire interval.

Figure 14:
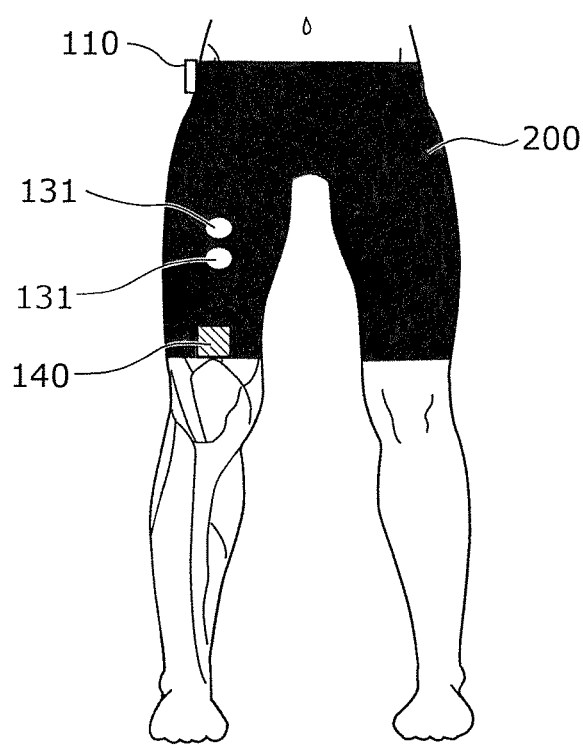
FIG. 14 is a diagram illustrating a subject wearing pants for risk-of-falling determination according to the embodiment.

FIG. 14 illustrates a subject wearing pants for risk-of-falling determination according to the embodiment.

The pants for risk-of-falling determination include the above-described risk-of-falling determination apparatus 100 and a pants portion 200. The pants portion 200 is knee-length pants that tightly fit the thighs. The risk-of-falling determination apparatus 100 is attached to the pants portion 200. The walk information obtaining unit 140 of the risk-of-falling determination apparatus 100 of this the pants for risk-of-falling determination is an acceleration sensor (hereinafter, referred to as an acceleration sensor 140).

When the user who is a subject wears the pants for risk-of-falling determination, the pair of first electrodes 131 are in contact with skin above the quadriceps femoris muscle (for example, the rectus femoris muscle) of a thigh of the user and the pair of second electrodes 132 are in contact with skin above the hamstrings muscle (for example, the biceps femoris muscle) of the thigh of the user. Further, the acceleration sensor 140 is fixed to the knee of the user when the user wears the pants for risk-of-falling determination.

The swing phase and the stance phase are detected by using the acceleration sensor fixed to the heel in the "1-6. Walking Cycle Detection Method" section; however, the swing phase and the stance phase are successfully detected also by using the acceleration sensor 140 fixed to the knee as illustrated in FIG. 14.

The acceleration sensor 140 fixed to the knee obtains, as the walk information, acceleration at the knee in the perpendicular direction (i.e., vertical direction). The stance phase identification unit 121 applies a low-pass filter as in the examples illustrated in FIGS. 3 and 4 and extracts peaks by using the threshold Th1 and Th2. Note that the frequency of the low-pass filter may be 3 Hz as in the "1-6. Walking Cycle Detection Method" section; however, any frequency other than 3 Hz may be used if the frequency is in a range of 3 Hz to 5 Hz and corresponds to a walking cycle of the detection target.

Figure 15:
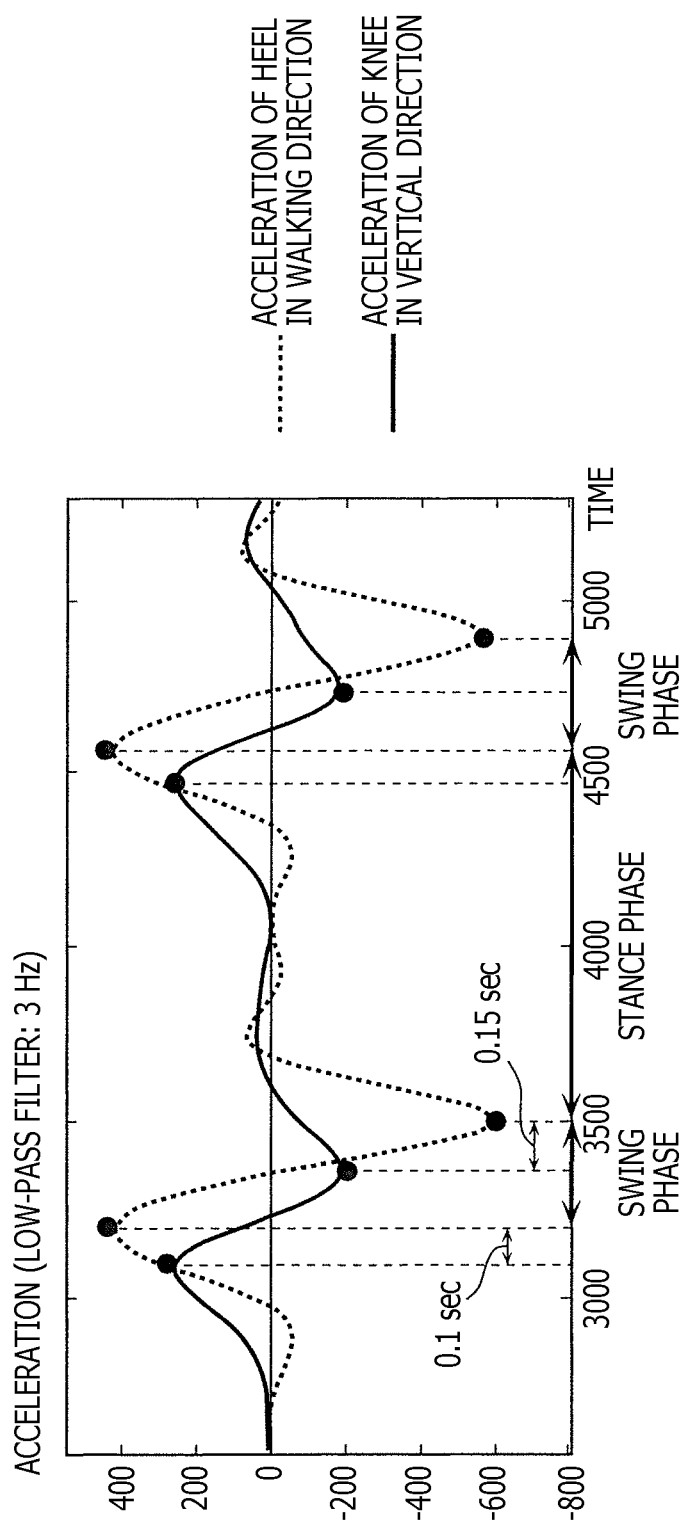
FIG. 15 is a diagram illustrating acceleration data obtained by an acceleration sensor attached to the heel and acceleration data obtained by an acceleration sensor attached to the knee during a walk in the embodiment.

FIG. 15 illustrates acceleration data obtained by acceleration sensors attached to the heel and the knee during a walk. The acceleration at the heel is positive when the heel is accelerated in the direction in which the user moves by walking, whereas the acceleration at the knee is positive when the knee is accelerated in the vertical upward direction. In addition, a 3 Hz low-pass filter is applied to the acceleration at the heel and the acceleration at the knee illustrated in FIG. 15. As illustrated in FIG. 15, a peak of the acceleration at the knee in the positive direction (i.e., local maximum) is at a timing earlier by approximately 100 ms than a timing of the closest peak of the acceleration at the heel in the positive direction (i.e., local maximum). Further, a peak of the acceleration at the knee in the negative direction (i.e., local minimum) is at a timing earlier by approximately 150 ms than a timing of the closest peak of the acceleration at the heel in the negative direction (i.e., local minimum).

It is considered that the peak of the acceleration at the knee and the peak of the acceleration at the heel change in proportion to the walking cycle (pitch). In the case of the acceleration data illustrated in FIG. 15, the walking cycle is 1360 ms/step. In addition, a delay of the timing of the positive peak of the acceleration at the heel relative to the timing of the positive peak of the acceleration at the knee is approximately 8%. A delay of the timing of the negative peak of the acceleration at the heel relative to the timing of the negative peak of the acceleration at the knee is approximately 11%. Accordingly, in the case of using the vertical-direction acceleration data of the knee, the stance phase identification unit 121 sets, as the starting point of the swing phase, a time point obtained by adding approximately 8% of the walking cycle to the time point of the extracted positive peak and sets, as the end point of the swing phase, a time point obtained by adding approximately 11% of the walking cycle to the time point of the extracted negative peak.

That is, the stance phase identification unit 121 of the pants for risk-of-falling determination identifies a first time point and a second time point in the predetermined time interval (for one step, for example). The first time point is a time point at which the acceleration that is greater than or equal to a second threshold indicates the local maximum. The second time point is a time point that is later than the first time point and at which the acceleration that is less than or equal to a third threshold indicates the local minimum. The stance phase identification unit 121 then performs correction on each of the first time point and the second time point on the basis of the walking cycle, and identifies, as the interval of the stance phase, a remaining interval obtained by excluding an interval from the corrected first time point to the corrected time point from the predetermined time interval. The acceleration sensor 140 may be attached to the heel. In this case, the stance phase identification unit 121 identifies, as the interval of the stance phase, a remaining interval obtained by excluding an interval from the first time point to the second time point from the predetermined time interval.

Figure 16:
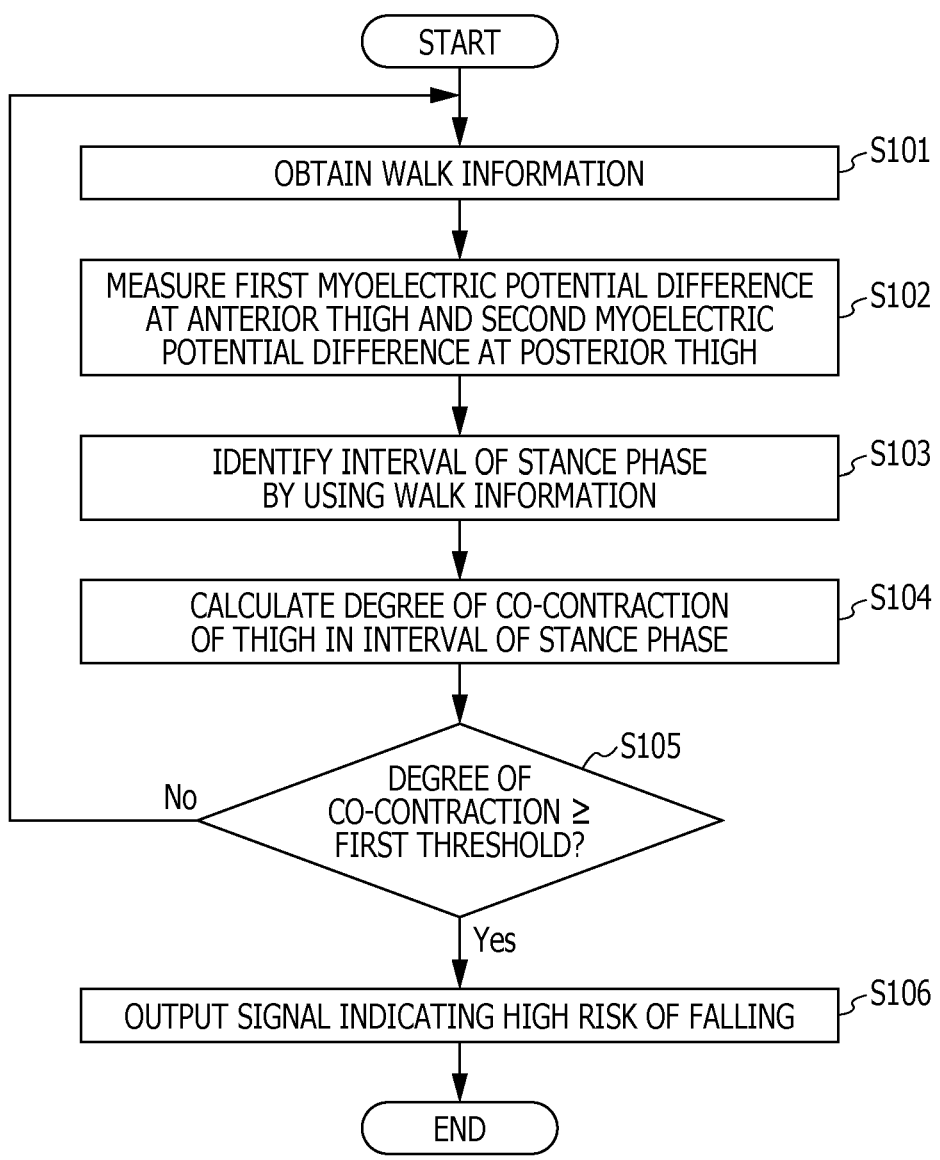
FIG. 16 is a flowchart illustrating an operation performed by the risk-of-falling determination apparatus according to the embodiment.

FIG. 16 is a flowchart illustrating an operation performed by the risk-of-falling determination apparatus 100 according to the embodiment.

In step S101, the walk information obtaining unit 140 obtains walk information of a user for a predetermined time interval.

In step S102, the myoelectric sensor 111 measures a first myoelectric potential difference, which is a myoelectric potential difference on the anterior surface of a thigh of a leg of the user, by using the pair of first electrodes 131 disposed on the anterior surface of the thigh. The myoelectric sensor 111 also measures a second myoelectric potential difference, which is a myoelectric potential difference on the posterior surface of the thigh of the leg of the user, by using the pair of second electrodes 132 disposed on the posterior surface of the thigh.

In step S103, the control circuit 120 identifies an interval of the stance phase in the predetermined time interval by using the walk information of the user. Here, the interval of the stance phase is an interval for which a foot of the leg of the user is in contact with the ground.

In step S104, the control circuit 120 calculates the degree of co-contraction at the leg of the user on the basis of the first and second myoelectric potential differences for the interval of the stance phase. Here, co-contraction refers to simultaneous activation of a muscle near the anterior surface of a thigh and a muscle near the posterior surface of the thigh.

In step S105, the control circuit 120 determines whether the degree of co-contraction is greater than or equal to a first threshold.

In step S106, the output unit 112 outputs a signal indicating that the user has a high risk of falling if the degree of co-contraction is greater than or equal to the first threshold.

Figure 17:
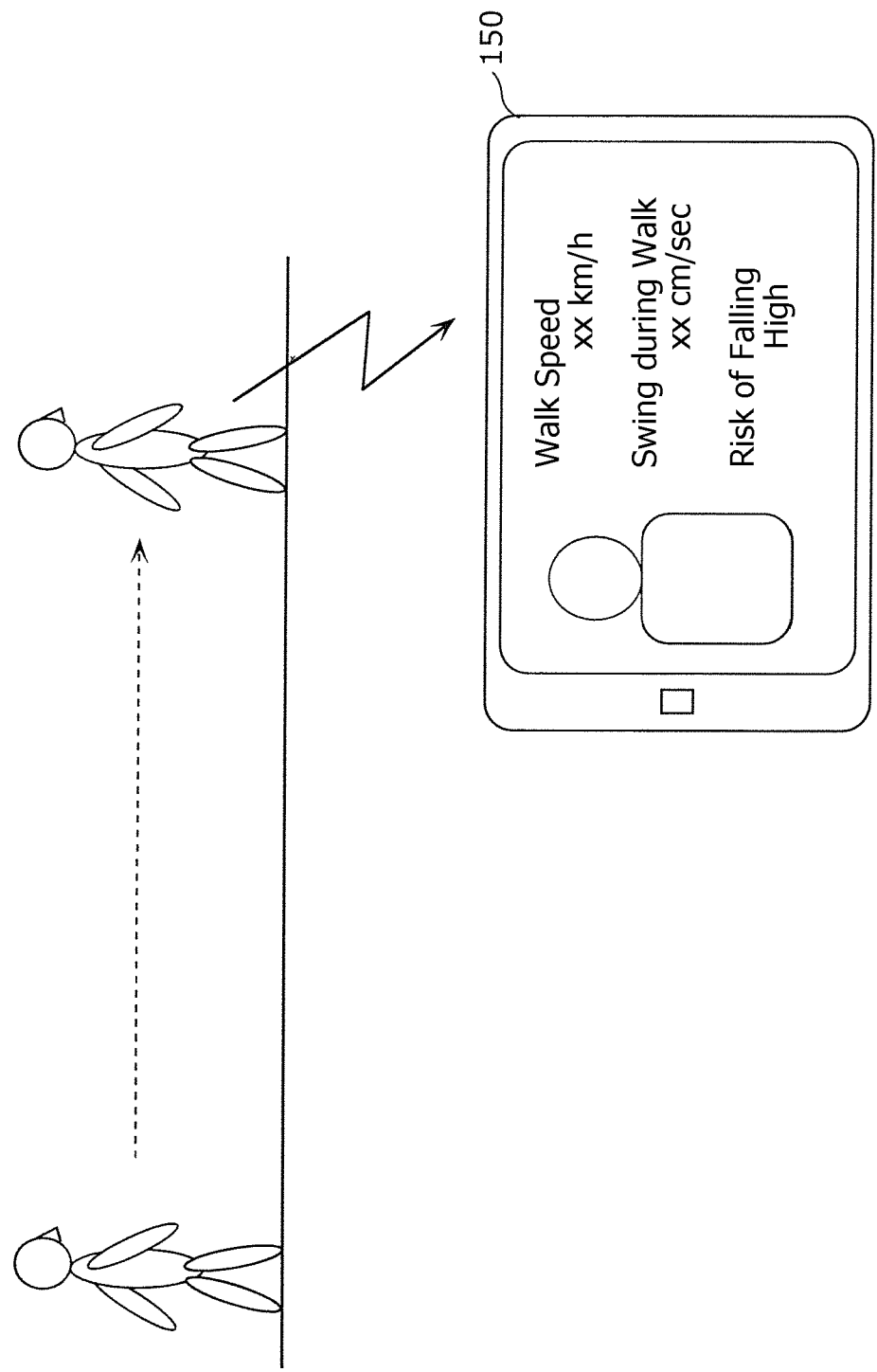
FIG. 17 is a diagram illustrating a situation in which the risk of falling is determined based on how a user wearing the pants for risk-of-falling determination according to the embodiment walks.

FIG. 17 illustrates a situation in which the risk of falling is determined based on walking of a user wearing the pants for risk-of-falling determination. In the example illustrated in FIG. 17, the user whose the risk of falling is to be determined wears the pants for risk-of-falling determination and walks a predetermined distance. The risk-of-falling determination apparatus 100 calculates the degree of co-contraction during the walk and determines whether the degree of co-contraction is greater than or equal to the first threshold. If the degree of co-contraction is greater than or equal to the first threshold, the risk-of-falling determination apparatus 100 transmits a signal indicating that the user has a high risk of falling to the terminal apparatus 150. Upon receipt of this signal, the terminal apparatus 150 displays an image including text indicating that the user has a high risk of falling. The user may walk while carrying the terminal apparatus 150 or may walk without carrying the terminal apparatus 150. If the user does not carry the terminal apparatus 150, the user is unable to recognize their the risk of falling by using the terminal apparatus 150. Accordingly, in this case, the processing unit 110 of the risk-of-falling determination apparatus 100 may include a speaker or beeper that emits sound in accordance with the signal and may notify the user that the user has a high risk of falling by the sound.

The steady walk determination unit 122 sometimes determines that there is no interval of the stance phase of steady walking. In such a case, the control circuit 120 of the risk-of-falling determination apparatus 100 may regularly output sound from the speaker or beeper to prompt the user to perform steady walking. With this configuration, the stability in the user's walk may be increased. In particular, it is possible to prompt the user to perform steady walking by outputting sound at the start timing of the stance phase of the user.

3. Brief Account

The risk-of-falling determination apparatus 100 according to the embodiment includes the walk information obtaining unit 140, the myoelectric sensor 111, the control circuit 120, and the output unit 112 as illustrated in FIG. 12.

Accordingly, the risk-of-falling determination apparatus 100 is capable of determining the user's risk of falling at an accuracy of 60% or higher as described in the "1-13. Summary of Findings Obtained from Experiment" section. In addition, since there is no need to use special physical strength data to determine the risk of falling, the risk of falling is successfully determined at the accuracy in such determination even for subjects having substantially the same physical strength data. Further, since the risk of falling is determined when the subject walks, the risk of falling is successfully determined in a simple manner without requiring the time and effort of the subject and the evaluator or the examiner. That is, the risk of falling can be determined simply with a high accuracy.

In other words, the risk of falling can be determined on the basis of co-contraction of lower-limb muscles at the thigh of the user during a simple walking task. Since no complicated tasks or the like are required, the risk of falling can be determined in any situation by figuring out an easier way to attach the myoelectric sensor or the like. As a result, the load imposed on the user can be decreased.

Since the risk-of-falling determination apparatus according to the embodiment is capable of determining the risk of falling by measuring myoelectric potential differences produced during a walk, physical strength measurement or the like is not needed. Accordingly, precautions against fall can be taken easily. In addition, the risk-of-falling determination apparatus allows a decrease in the balancing function which occurs in relation to aging or the like to be discovered at an early stage and can be utilized to consider a rehabilitation program. For example, the risk-of-falling determination apparatus can be used not only at a rehabilitation facility but also at a home and can be incorporated into a rehabilitation apparatus that can be easily used at a home.

While the risk-of-falling determination apparatus according to one or a plurality of aspects has been described above on the basis of the embodiment, the present disclosure is not limited to the embodiment. Various modifications of the embodiment conceived by a person skilled in the art and embodiments obtained by combining elements of different embodiments with each other may also be within the scope of the one or plurality of aspects as long as such modifications and embodiments do not depart from the essence of the present disclosure.

All or some of the units or devices, or all or some of the functional blocks of the block diagrams illustrated in FIGS. 12 and 13 may be implemented by one or one or more electronic circuits including a semiconductor device, a semiconductor integrated circuit (IC), or a large scale integration (LSI). The LSI or IC may be implemented by one chip or may be implemented by a combination of a plurality of chips. For example, functional blocks other than the storage element may be integrated on one chip. Although the term "LSI" or "IC" is used herein, the name changes depending on the degree of integration and the term "system LSI", "very large scale integration (VLSI)", or "ultra large scale integration (ULSI)" may be used. A field programmable gate array (FPGA) that is programmable after production of the LSI or a reconfigurable logic device in which connections within the LSI is reconfigurable and setup of circuit cells within the LSI are possible may be used for the same purpose.

Further, all or some of functions or operations of the units, the apparatuses, and part of the apparatuses can be implemented by software-based processing. In this case, the software is stored on one or one or more non-transitory recoding media, such as a ROM, an optical disc, or a hard disk drive. When the software is executed by a processing device (processor), the software causes the processing device (processor) and its peripheral devices to carry out a specific function included in the software. A system or apparatus may include one or one or more non-transitory recording media storing the software, the processing device (processor), and necessary hardware devices, for example, an interface.

In addition, each of the components of the embodiment may be implemented by dedicated hardware or by executing a software program suitable for the component. Each of the components may be implemented as a result of a program executor, such as a CPU or processor, reading and executing a software program stored on a recording medium, such as a hard disk or semiconductor memory. Software that implements the risk-of-falling determination apparatus according to the embodiment is a program that causes a computer to perform each of the steps included in the flowchart illustrated in FIG. 16, for example.

The risk-of-falling determination apparatus according to an aspect of the present disclosure successfully determines the user's risk of falling simply with a high accuracy and is applicable to, for example, nursing-care equipment and rehabilitation apparatus for elderly people.

What is claimed is:

1. A risk-of-falling determination apparatus comprising:
    a walk information obtainer that obtains walk information of a user for a predetermined time interval, the walk information including a plurality of steps of the user;
    a myoelectric sensor that measures first myoelectric potential differences by using first electrodes configured to be disposed on an anterior surface of a thigh of a leg of the user and measures second myoelectric potential differences by using second electrodes configured to be disposed on a posterior surface of the thigh of the leg of the user;
    a control circuit that
        excludes a first step of the user and a last step of the user from the predetermined time interval to obtain a period of steady walking of the user, the first step of the user and the last step of the user being included in the plurality of steps of the walk information of the user,
        identifies an interval of a stance phase in the predetermined time interval by using the walk information of the user, the interval of the stance phase being an interval for which a foot of the leg of the user is in contact with ground, the interval of the stance phase being included in the period of steady walking of the user, (ii) calculates a degree of co-contraction of a muscle at the leg of the user by using the first myoelectric potential differences for the interval of the stance phase and the second myoelectric potential differences for the interval of the stance phase, the co-contraction being simultaneous activation of a muscle near the anterior surface of the thigh of the leg and a muscle near the posterior surface of the thigh of the leg, and
        compares the degree of co-contraction to a first threshold; and
    an outputter that outputs a signal indicating that the user has a high risk of falling when the degree of co-contraction is greater than or equal to the first threshold.

2. The risk-of-falling determination apparatus according to claim 1,
    wherein the walk information obtainer is an acceleration sensor that is configured to be disposed on the leg of the user and that is configured to measure acceleration at the leg of the user for the predetermined time interval, and
    wherein the control circuit identifies the interval of the stance phase in the predetermined time interval on the basis of a value of the acceleration.

3. The risk-of-falling determination apparatus according to claim 2,
    wherein the control circuit identifies a first time point and a second time point in the predetermined time interval,
    wherein the first time point is a time point at which (i) the acceleration that is greater than or equal to a second threshold and (ii) a local maximum of the acceleration occurs in the predetermined time interval,
    wherein the second time point is a time point that is later than the first time point and the second time point is the time point at which (i) the acceleration that is smaller than or equal to a third threshold and (ii) a local minimum of the acceleration occurs in the predetermined time interval, and
    wherein the control circuit identifies, as the interval of the stance phase, an interval based on (i) a time period from the first time point to the second time point or (ii) a remaining interval obtained by excluding the interval based on the time period from first time point to the second time point from the predetermined time interval.

4. The risk-of-falling determination apparatus according to claim 3,
    wherein the control circuit determines that the remaining interval is the interval of the stance phase when the acceleration is positive acceleration, and wherein the positive acceleration is acceleration produced when the leg of the user is accelerated in a direction in which the user moves by walking.

5. The risk-of-falling determination apparatus according to claim 1,
wherein the walk information obtainer is a footswitch configured to be disposed on a back of the foot of the user, and
wherein the control circuit identifies an interval for which the footswitch is on, the interval for which the footswitch is on being the interval of the stance phase in the predetermined time interval.

6. A risk-of-falling determination method comprising:
obtaining, using a walk information obtainer, walk information of a user for a predetermined time interval, the walk information including a plurality of steps of the user;
measuring, using a myoelectric sensor, first myoelectric potential differences by using first electrodes configured to be disposed on an anterior surface of a thigh of a leg of the user and second myoelectric potential differences by using second electrodes configured to be disposed on a posterior surface of the thigh of the leg of the user;
excluding, using a control circuit, a first step of the user and a last step of the user from the predetermined time interval to obtain a period of steady walking of the user, the first step of the user and the last step of the user being included in the plurality of steps of the walk information of the user;
identifying, using the control circuit, an interval of a stance phase in the predetermined time interval by using the walk information of the user, the interval of the stance phase being an interval for which a foot of the leg of the user is in contact with ground, the interval of the stance phase being included in the period of steady walking of the user;
calculating, using the control circuit, a degree of co-contraction of a muscle at the leg of the user by using the first myoelectric potential differences for the interval of the stance phase and the second myoelectric potential differences for the interval of the stance phase, the co-contraction being simultaneous activation of a muscle near the anterior surface of the thigh of the leg and a muscle near the posterior surface of the thigh of the leg;
comparing, using the control circuit, the degree of co-contraction to a first threshold; and
outputting, using an outputter, a signal indicating that the user has a high risk of falling when the degree of co-contraction is greater than or equal to the first threshold.

7. The risk-of-falling determination method according to claim 6,
wherein the walk information of the user for the predetermined time interval is obtained by using an acceleration sensor that is configured to be disposed on the leg of the user and that is configured to measure acceleration at the leg of the user for the predetermined time interval, and
wherein the interval of the stance phase in the predetermined time interval is identified based on a value of the acceleration.

8. The risk-of-falling determination method according to claim 7,
wherein in the identifying the interval of the stance phase, a first time point and a second time point in the predetermined time interval are identified,
wherein the first time point is a time point at which (i) the acceleration that is greater than or equal to a second threshold and (ii) a local maximum of the acceleration occurs in the predetermined time interval,
wherein the second time point is a time point that is later than the first time point and the second time point is the time point at which (i) the acceleration that is smaller than or equal to a third threshold and (ii) a local minimum of the acceleration occurs in the predetermined time interval, and
wherein in the identifying the interval of the stance phase, an interval based on (i) a time period from the first time point to the second time point or (ii) a remaining interval obtained by excluding the interval based on the time period from the first time point to the second time point from the predetermined time interval is identified as the interval of the stance phase.

9. The risk-of-falling determination method according to claim 8,
wherein the remaining interval is determined to be the interval of the stance phase when the acceleration is positive acceleration, and
wherein the positive acceleration is acceleration produced when the leg of the user is accelerated in a direction in which the user moves by walking.

10. The risk-of-falling determination method according to claim 6,
wherein the walk information of the user for the predetermined time interval is obtained by using a footswitch configured to be disposed on a back of the foot of the user, and
wherein an interval for which the footswitch is on is identified, the interval for which the footswitch being on the interval of the stance phase in the predetermined time interval.

11. A recording medium storing a control program for causing a device including a processor to perform a process, the recording medium being a non-volatile computer-readable recording medium, the process comprising:
obtaining, using a walk information obtainer, walk information of a user for a predetermined time interval, the walk information including a plurality of steps of the user;
measuring, using a myoelectric sensor, first myoelectric potential differences by using first electrodes configured to be disposed on an anterior surface of a thigh of a leg of the user and second myoelectric potential differences by using second electrodes configured to be disposed on a posterior surface of the thigh of the leg of the user;
excluding, using a control circuit, a first step of the user and a last step of the user from the predetermined time interval to obtain a period of steady walking of the user, the first step of the user and the last step of the user being included in the plurality of steps of the walk information of the user;
identifying, using the control circuit, an interval of a stance phase in the predetermined time interval by using the walk information of the user, the interval of the stance phase being an interval for which a foot of the leg of the user is in contact with ground, the interval of the stance phase being included in the period of steady walking of the user;

calculating, using the control circuit, a degree of co-contraction of a muscle at the leg of the user by using the first myoelectric potential differences for the interval of the stance phase and the second myoelectric potential differences for the interval of the stance phase, the co-contraction being simultaneous activation of a muscle near the anterior surface of the thigh of the leg and a muscle near the posterior surface of the thigh of the leg;

comparing, using the control circuit, the degree of co-contraction to a first threshold; and outputting, using an outputter, a signal indicating that the user has a high risk of falling when the degree of co-contraction is greater than or equal to the first threshold.

* * * * *